(12) United States Patent
Hilaly et al.

(10) Patent No.: US 8,177,980 B2
(45) Date of Patent: May 15, 2012

(54) SEPARATION OF A MIXTURE OF POLYHYDRIC ALCOHOLS

(75) Inventors: Ahmad K. Hilaly, Forsyth, IL (US); Robert Duane Sandage, Decatur, IL (US); John G. Soper, Mt. Zion, IL (US)

(73) Assignee: Archer Daniels Midland Company, Decatur, IL (US)

( * ) Notice: Subject to any disclaimer, the term of this patent is extended or adjusted under 35 U.S.C. 154(b) by 616 days.

(21) Appl. No.: 12/235,192

(22) Filed: Sep. 22, 2008

(65) Prior Publication Data

US 2009/0120878 A1 May 14, 2009

Related U.S. Application Data

(60) Provisional application No. 60/986,827, filed on Nov. 9, 2007.

(51) Int. Cl.
*B01D 15/08* (2006.01)

(52) U.S. Cl. ...... 210/659; 210/635; 210/656; 210/198.2

(58) Field of Classification Search ................ 210/635, 210/656, 659, 198.2
See application file for complete search history.

(56) References Cited

U.S. PATENT DOCUMENTS

| | | | |
|---|---|---|---|
| 2,985,589 A | 5/1961 | Broughton et al. | |
| 3,040,777 A | 6/1962 | Carson et al. | |
| 3,422,848 A | 1/1969 | Liebman et al. | |
| 3,706,812 A | 12/1972 | Derosset et al. | |
| 4,402,832 A | 9/1983 | Gerhold | |
| 4,476,331 A | 10/1984 | Dubeck et al. | |
| 4,478,721 A | 10/1984 | Gerhold | |
| 4,642,394 A | 2/1987 | Che | |
| 4,642,397 A | 2/1987 | Zinnen et al. | |
| 4,935,102 A | 6/1990 | Berg | |
| 4,966,658 A * | 10/1990 | Berg | 203/62 |
| 5,107,018 A | 4/1992 | Schuster | |
| 5,206,927 A | 4/1993 | Finzel et al. | |
| 5,214,219 A | 5/1993 | Casale et al. | |
| 5,276,181 A | 1/1994 | Casale et al. | |
| 5,423,955 A | 6/1995 | Berg | |
| 5,432,955 A | 7/1995 | Plotka et al. | |
| 5,616,817 A | 4/1997 | Schuster et al. | |
| 6,291,725 B1 | 9/2001 | Chopade et al. | |
| 2002/0056686 A1 * | 5/2002 | Kyrlidis et al. | 210/656 |
| 2002/0133049 A1 * | 9/2002 | Hilaly et al. | 568/872 |

(Continued)

FOREIGN PATENT DOCUMENTS

EP 0 415 202 A2 3/1991

(Continued)

OTHER PUBLICATIONS

Product Information Lewatit AF-5, May 5, 2007.*

(Continued)

*Primary Examiner* — Ernest G Therkorn
(74) *Attorney, Agent, or Firm* — William B. Miller

(57) ABSTRACT

The present invention provides methods of separating at butanediol compound from a mixture containing polyhydric alcohols and butanediol compounds. The mixture of polyhydric alcohols typically contains propylene glycol and ethylene glycol in addition to the butanediol contaminants. Butanediol contaminants are removed by contacting the mixture with a chromatographic matrix. Either the butanediol compounds or the non-butanediol compounds adsorb to the chromatographic matrix. If desired, the adsorbed compounds may be eluted from the matrix, purified and used in products.

18 Claims, 17 Drawing Sheets

U.S. PATENT DOCUMENTS

| | | | |
|---|---|---|---|
| 2005/0045560 A1 | 3/2005 | Boyd et al. | |
| 2005/0161401 A1* | 7/2005 | Heikkila et al. | 210/656 |
| 2008/0275277 A1* | 11/2008 | Kalagias | 568/854 |
| 2010/0022740 A1* | 1/2010 | Okazaki et al. | 528/271 |

FOREIGN PATENT DOCUMENTS

| | | |
|---|---|---|
| EP | 0 523 014 A2 | 1/1993 |

OTHER PUBLICATIONS

PTO Translation No. 11-3545 of Gunzel, Adsorption of Diols from Fermatation Media onto Hydrophobic Zeolites.*

Lanxess, Undated.*

Crabtree, S.P., et al., "Optimize glycol production from biomass. A novel glycol production method provides a way to use glycerol-the unwanted byproduct from biodiesel processing," in *Hydrocarbon Processing*, pp. 87-92 (Feb. 2006).

Günzel, B., et al., "Adsorption von Diolen aus Fermentationsmedien en hydrophobe Zeolithe," *Chem. Ing. Tech.* 62:748-750, VCH Verlagsgesellschaft mbH (1990).

Hanko, V.P., et al., "Determination of Carbohydrates, Sugar Alcohols, and Glycols in Cell Cultures and Fermentation Broths Using High-Performance Anion-Exchange Chromatography with Pulsed Amperometric Detection," *Anal. Biochem.* 283:192-199, Academic Press (2000).

Kim, J.W., et al., "Adsorption of 2,3-butanediol on Si(1 0 0)," *Surf. Sci.* 559:179-185, Elsevier B.V. (2004).

Kusunoki, Y., et al., "Highly active metal-acid bifunctional catalyst system for hydrogenolysis of glycerol under mild reaction conditions," *Catal. Commun.* 6:645-649, Elsevier Ltd. (2005).

Miyazawa, T., et al., "Glycerol conversion in the aqueous solution under hydrogen over Ru/C + an ion-exchange resin and its reaction mechanism," *J. Catal.* 240:213-221, Elsevier Inc. (Mar. 2006).

Montassier, C., et al., "Polyol Conversion by Liquid Phase Heterogenous Catalysis over Metals," *Heterogenous Catalysis and Fine Chemicals* 41:165-170, Elsevier Science Publishers B.V. (1988).

Montassier, C., et. al., "Polyol conversions into furanic derivatives on bimetallic catalysts: Cu-Ru, Cu-Pt and Ru-Cu," *J. Mol. Catal.* 70:65-84, Elsevier Sequoia, Lausanne (1991).

Montassier, C., et al., "Deactivation of supported copper based catalysts during polyol conversion in aqueous phase," *Appl. Catal. A: General* 121:231-244, Elsevier Science B.V. (1995).

Perosa, A., and Tundo, P., "Selective Hydrogenolysis of Glycerol with Raney Nickel," *Ind. Eng. Chem. Res.* 44:8535-8537, American Chemical Society (2005).

International Search Report for International Application No. PCT/US2008/011214, European Patent Office, Netherlands, mailed on Mar. 27, 2009.

Derwent Patent Abstract, English language abstract for EP 0 415 202 A2 (listed as document FP1 on accompanying form PTO/SB/08A).

The DOW Chemical Company, Dow Propylene Glycol USP/EP, Purity Plus, Form No. 117-00974-700AMS, 23 pages, published Apr. 2000.

Propylene, The United States Pharmacopeia, pp. 1850, The United States Pharmacopeial Convention, Jan. 1, 2006.

Title 7, Agriculture, Chapter 107 Renewable Energy Research and Development, Sec. 7USC8102, Federal procurement of biobased products, Jan. 20, 2004, 5 pages, The U.S. Code Online via GPO accessed online via www.access.gpo.gov.

Indian Patent Application No. 1262/DEL/94, Indian Patent Specification, Provisional Specification, 14 pages, filed on May 10, 1994.

* cited by examiner

NON-FUNCTIONAL RESIN PULSE TEST OF PG REACTOR PRODUCT
RESIN: Dow V493

| FRACTION SIZE: | 8 MLS | TEMPERATURE: | 45C | Feed NOT SPIKED with BDO |
| COLUMN SIZE: | 100 MLS | FLOW RATE: | 3 MLS/MIN | |
| PULSE SIZE: | 10 MLS | | | |

| FRAC. NO. | BV | PG % | 1,2 BDO % | 2,3 BDO % | Glycerol % | EG % | Lactic % | DEG % | Na ppm | Na % | Ce/Cf PG | Ce/Cf 1,2 BDO | Ce/Cf 2,3 BDO | Ce/Cf Glycerol | Ce/Cf EG | Ce/Cf Lactic | Ce/Cf DEG | Ce/Cf Na | |
|---|---|---|---|---|---|---|---|---|---|---|---|---|---|---|---|---|---|---|---|
| 1 | 0.08 | 0.02 | 0.00 | 0.00 | 0.00 | 0.00 | 0 | 0 | 14.23 | 0.001423 | 0.001 | 0.000 | 0.000 | 0.000 | 0.000 | 0 | #DIV/0! | 0.002 | diH2O elution |
| 3 | 0.24 | 0.00 | 0.00 | 0.00 | 0.00 | 0.00 | 0 | 0 | 12.42 | 0.001242 | 0.000 | 0.000 | 0.000 | 0.000 | 0.000 | 0 | #DIV/0! | 0.002 | |
| 5 | 0.40 | 0.00 | 0.00 | 0.00 | 0.00 | 0.00 | 0.353 | 0 | 20.22 | 0.002022 | 0.000 | 0.000 | 0.000 | 0.000 | 0.000 | 0.150212766 | #DIV/0! | 0.003 | |
| 7 | 0.56 | 0.00 | 0.02 | 0.00 | 0.00 | 0.00 | 0.608 | 0 | 94.90 | 0.00949 | 0.000 | 0.065 | 0.000 | 0.000 | 0.000 | 0.258723404 | #DIV/0! | 0.016 | |
| 9 | 0.72 | 0.00 | 0.06 | 0.00 | 0.00 | 0.00 | 1.104 | 0 | 2152.00 | 0.2152 | 0.000 | 0.190 | 0.000 | 0.000 | 0.000 | 0.469787234 | #DIV/0! | 0.371 | |
| 11 | 0.88 | 0.00 | 0.02 | 0.00 | 0.04 | 0.13 | 0.67 | 0 | 954.00 | 0.0954 | 0.000 | 0.071 | 0.000 | 0.260 | 0.087 | 0.285106383 | #DIV/0! | 0.164 | |
| 13 | 1.04 | 0.38 | 0.00 | 0.00 | 0.06 | 0.55 | 0 | 0 | 144.60 | 0.01446 | 0.015 | 0.000 | 0.000 | 0.367 | 0.368 | 0 | #DIV/0! | 0.025 | |
| 15 | 1.20 | 2.88 | 0.00 | 0.00 | 0.02 | 0.33 | 0 | 0 | 51.50 | 0.00515 | 0.113 | 0.000 | 0.000 | 0.120 | 0.223 | 0 | #DIV/0! | 0.009 | |
| 17 | 1.36 | 4.02 | 0.00 | 0.00 | 0.00 | 0.08 | 0 | 0 | 33.99 | 0.003399 | 0.158 | 0.000 | 0.000 | 0.000 | 0.050 | 0 | #DIV/0! | 0.006 | |
| 19 | 1.52 | 3.37 | 0.00 | 0.00 | 0.00 | 0.02 | 0 | 0 | 25.41 | 0.002541 | 0.132 | 0.000 | 0.000 | 0.000 | 0.013 | 0 | #DIV/0! | 0.004 | |
| 21 | 1.68 | 2.48 | 0.00 | 0.00 | 0.00 | 0.00 | 0 | 0 | 22.91 | 0.002291 | 0.097 | 0.000 | 0.000 | 0.000 | 0.000 | 0 | #DIV/0! | 0.004 | |
| 23 | 1.84 | 1.74 | 0.00 | 0.00 | 0.00 | 0.00 | 0 | 0 | 22.05 | 0.002205 | 0.068 | 0.000 | 0.000 | 0.000 | 0.000 | 0 | #DIV/0! | 0.004 | |
| 25 | 2.00 | 1.23 | 0.00 | 0.00 | 0.00 | 0.00 | 0 | 0 | 19.51 | 0.001951 | 0.049 | 0.000 | 0.000 | 0.000 | 0.000 | 0 | #DIV/0! | 0.000 | switch to MeOH elution |
| 27 | 2.16 | 0.81 | 0.00 | 0.00 | 0.00 | 0.00 | 0 | 0 | 18.43 | 0.001843 | 0.032 | 0.000 | 0.000 | 0.000 | 0.000 | 0 | #DIV/0! | 0.003 | |
| 29 | 2.32 | 0.50 | 0.00 | 0.03 | 0.00 | 0.00 | 0 | 0 | 18.61 | 0.001861 | 0.020 | 0.000 | 0.015 | 0.000 | 0.000 | 0 | #DIV/0! | 0.003 | |
| 31 | 2.48 | 0.32 | 0.00 | 0.02 | 0.00 | 0.00 | 0 | 0 | 16.56 | 0.001656 | 0.013 | 0.000 | 0.013 | 0.000 | 0.000 | 0 | #DIV/0! | 0.003 | |
| 33 | 2.64 | 0.20 | 0.00 | 0.02 | 0.00 | 0.00 | 0 | 0 | 14.29 | 0.001429 | 0.008 | 0.000 | 0.014 | 0.000 | 0.000 | 0 | #DIV/0! | 0.002 | |
| 35 | 2.80 | 0.12 | 0.00 | 0.02 | 0.00 | 0.00 | 0 | 0 | 13.19 | 0.001319 | 0.005 | 0.000 | 0.013 | 0.000 | 0.000 | 0 | #DIV/0! | 0.002 | |
| 37 | 2.96 | 0.12 | 0.18 | 1.14 | 0.00 | 0.00 | 0 | 0 | | | 0.005 | 0.565 | 0.690 | 0.000 | 0.000 | 0 | #DIV/0! | 0.000 | |
| 39 | 3.12 | 0.02 | 0.03 | 0.15 | 0.00 | 0.00 | 0 | 0.031 | | | 0.001 | 0.106 | 0.093 | 0.000 | 0.000 | 0 | #DIV/0! | 0.000 | |
| FEED | n/a | 25 | 0.31 | 1.65 | 0.15 | 1.49 | 2.35 | 0 | 5806 | 0.5806 | | | | | | | | | |

FIG. 9

SEPARATION OF A MIXTURE OF POLYHYDRIC ALCOHOLS

FIELD OF THE INVENTION

The present invention relates to methods of separating mixtures of polyhydric alcohols. In particular, the invention relates to methods of separating butanediol compounds, particularly 1,2-butanediol and 2,3-butanediol from a mixture of polyhydric alcohols using a chromatographic matrix. The invention also relates to a simulated moving bed apparatus for use in the methods of the present invention.

BACKGROUND OF THE INVENTION

Typically, propylene glycol and ethylene glycol are produced from petrochemical sources. For example, commercial production of propylene glycol involves the hydration of propylene oxide, which is made by the oxidation of propylene. Similarly, commercial production of ethylene glycol involves the hydration of ethylene oxide, made by the oxidation of ethylene. Both propylene and ethylene are industrial by-products of gasoline manufacture; for example, they are by-products of fluid cracking of gas oils or steam cracking of hydrocarbons.

The world's supply of petroleum is being depleted at an increasing rate. Eventually, demand for petrochemical derived products will outstrip the supply of available petroleum. When this occurs, the market price of petroleum and, consequently, petroleum derived products will likely increase, making products derived from petroleum more expensive and less desirable. As the available supply of petroleum decreases, alternative sources and, in particular, renewable sources of comparable products will necessarily have to be developed. One potential renewable source of petroleum derived products is products derived from bio-based matter, such as agricultural and forestry products. Use of bio-based products may potentially counteract, at least in part, the problems associated with depletion of the petroleum supply.

In an effort to diminish dependence on petroleum products the United States government enacted the Farm Security and Rural Investment Act of 2002, section 9002 (7 U.S.C. 8102), hereinafter "FRISA", which requires federal agencies to purchase bio-based products for all items costing over $10,000. In response, the United States Department of Agriculture ("USDA") has developed Guidelines for Designating Bio-based Products for Federal Procurement (7 C.F.R. §2902) to implement FRISA, including the labeling of bio-based products with a "U.S.D.A. Certified Bio-based Product" label.

Propylene glycol that is produced by hydrogenolysis of a polyol, such as a carbohydrate, is referred to as bio-based propylene glycol. Propylene glycol that is produced by hydrogenolysis of glycerol, which in turn is obtained as a by product of biodiesel production from fats and oils obtained from animal, fungal, or plant sources, is referred to as bio-based propylene glycol.

FRISA has established certification requirements for determining bio-based content. These methods require the measurement of variations in isotopic abundance between bio-based products and petroleum derived products, for example, by liquid scintillation counting, accelerator mass spectrometry, or high precision isotope ratio mass spectrometry. Isotopic ratios of the isotopes of carbon, such as the $^{13}C/^{12}C$ carbon isotopic ratio or the $^{14}C/^{12}C$ carbon isotopic ratio, can be determined using isotope ratio mass spectrometry with a high degree of precision. Studies have shown that isotopic fractionation due to physiological processes, such as, for example, $CO_2$ transport within plants during photosynthesis, leads to specific isotopic ratios in natural or bio-derived compounds. Petroleum and petroleum derived products have a different $^{13}C/^{12}C$ carbon isotopic ratio due to different chemical processes and isotopic fractionation during the generation of petroleum. In addition, radioactive decay of the unstable $^{14}C$ carbon radioisotope leads to different isotope ratios in bio-based products compared to petroleum products. Bio-based content of a product may be verified by ASTM International Radioisotope Standard Method D 6866. ASTM International Radioisotope Standard Method D 6866 determines bio-based content of a material based on the amount of bio-based carbon in the material or product as a percent of the weight (mass) of the total organic carbon in the material or product. Both bio-derived and bio-based products will have a carbon isotope ratio characteristic of a biologically derived composition.

Biology offers an attractive alternative for industrial manufacturers looking to reduce or replace their reliance on petrochemicals and petroleum derived products. The replacement of petrochemicals and petroleum derived products with products and/or feed stocks derived from biological sources (i.e., bio-based products) offer many advantages. For example, products and feed stocks from biological sources are typically a renewable resource. As the supply of easily extracted petrochemicals continues to be depleted, the economics of petrochemical production will likely force the cost of the petrochemicals and petroleum derived products to higher prices compared to bio-based products. In addition, companies may benefit from the marketing advantages associated with bio-derived products from renewable resources in the view of a public becoming more concerned with the supply of petrochemicals.

Propylene glycol and ethylene glycol, both of which are polyols, can be produced from petroleum or from mixtures of carbohydrates via various commercial processes. for example, a number of commercial processes that produce polyols from complex mixtures of carbohydrates exist. These processes usually produce a homologous series of glycols. Some of the resulting polyols boil so close to one another that their separation by ordinary rectification is difficult. The relative volatility is so low that a large number of theoretical plates are required to produce high purity polyols.

In a process involving hydrocracking of higher carbohydrates, such as glucose, sorbitol or sucrose, the molecule is broken into fragments of lower molecular weight to form compounds which belong to the glycol or polyol family. For instance, U.S. Pat. No. 5,206,927 describes a homogeneous process for hydrocracking carbohydrates in the presence of soluble, transition metal catalyst with the production of lower polyhydric alcohols. A carbohydrate is contacted with hydrogen in the presence of a soluble transition metal catalyst and a strong base at a temperature of from about 25° C. to about 200° C. and a pressure of from about 15 to about 3000 psi. However, as is evident from Tables II and III in the disclosure of U.S. Pat. No. 5,206,927, about 2-7% of other polyol compounds are produced in the hydrocracking process.

FRISA underscores the importance to the US government since 2002 of making use of biobased products, where such exist. The present disclosure teaches method for meeting the need for several chemicals of biological origin by producing product streams enriched in propylene glycol, ethylene glycol, 1,2-butanediol and 1,3-butanediol. In this manner, the present disclosure makes available several biobased chemicals to satisfy the need for biobased chemicals.

Other processes describe that, in presence of gaseous hydrogen, and metallic catalysts, glycerol can be converted to propylene glycol; 1,3 propanediol; or ethylene glycol.

U.S. Pat. Nos. 5,276,181 and 5,214,219 describe a process of hydrogenolysis of glycerol using copper and zinc catalyst in addition to sulfided ruthenium catalyst at a pressure over 2100 psi and temperature between 240-270° C. Similarly, U.S. Pat. No. 5,616,817 describes a process of preparing 1,2 propanediol by catalytic hydrogenolysis of glycerol at elevated temperature and pressure using a catalyst comprising the metals cobalt, copper, manganese and molybdenum. German patent DE 541362 describes the hydrogenolysis of glycerol with a Nickel catalyst, while U.S. Pat. No. 4,476,331 describes a two stage method of hydrocracking carbohydrates (for example glucose), wherein a modified ruthenium catalyst is used for hydrocracking sorbitol to produce glycerol derivatives. European Patent applications EP-A-0523 014 and EP-A-0 415 202 describe a process for preparing lower polyhydric alcohols by catalytic hydrocracking of aqueous sucrose solutions at elevated temperature and pressure using a catalyst whose active material comprises the metals cobalt, copper and manganese. Persoa & Tundo (Ind. Eng. Chem. Res. 2005, 8535-8537) describe a process for converting glycerol to 1,2-propanediol by heating under low hydrogen pressure in presence of Raney nickel and a liquid phosphonium salt. Selectivities toward 1,2-propanediol as high as 93% were reported, but required using a pure glycerol and long reaction times (20 hrs). Crabtree et al. (Hydrocarbon Processing February 2006 pp 87-92) describe a phosphine/precious metal salt catalyst that permits a homogenous catalyst composition for converting glycerol into 1,2-propanediol. However, low selectivity (20-30%) was reported. Other reports indicate use of Raney copper (Montassier et al. *Bull. Soc. Chim. Fr.* 2 1989 148; Stud. Surf. Sci. Catal. 41 1988 165), copper on carbon (Montassier et al., *J. Appl. Catal. A* 121 1995 231)), copper-platinum and copper ruthenium (Montassier et al. *J. Mol. Catal.* 70 1991 65). Other homogenous catalyst compositions such as tungsten and Group VIII metal-containing catalyst compositions have been also tried (U.S. Pat. No. 4,642,394). Miyazawa et al. (*J. Catal.* 240 2006 213-221) & Kusunoki et al (*Catal. Comm.* 62005 645-649) describe a Ru/C and ion exchange resin for conversion of glycerol in aqueous solution. Again their process however, results in low conversions of glycerol (0.9-12.9%). The present disclosure overcomes the limitations of these disclosures by providing a means to enrich product streams in propylene glycol ethylene glycol, 1,2-butanediol and 1,3-butanediol.

One of the problems of producing glycerol derivatives by hydrogenolysis of glycerol is that other diol compounds are formed which reduce the purity of the desired component. For instance, in hydrocracking of higher carbohydrates such as, for example, sorbitol to produce propylene glycol, typically 3-5% by weight of 2,3-butanediol is produced in addition to 1,2-butanediol, ethylene glycol and 1,3-butanediol. These products are referred to as "polyols" or "polyhydric alcohols". The boiling points of these components as shown in Table 1 are very close to one another such that in a rectification column, either under atmospheric, reduced pressure or at an elevated pressure, the separation of substantially pure propylene glycol is difficult to attain.

TABLE 1

Polyols produced by Hydrocracking of Sorbitol

| Polyol | Weight Percent | Boiling Point, ° C. |
|---|---|---|
| 2,3-Butanediol | 3.5 | 182 |
| Propylene glycol | 16.5 | 187 |
| 1,2-Butanediol | 2.0 | 192 |
| Ethylene glycol | 25.2 | 198 |
| 1,3-Butanediol | 2.7 | 206 |
| 2,3-Hexanediol | — | 206 |
| 1,2-Pentanediol | — | 210 |
| 1,4-Pentanediol | — | 220 |
| 1,4-Butanediol | 2.1 | 230 |
| 1,5-Pentanediol | 0.1 | 242 |
| Diethylene glycol | 2.2 | 245 |
| 1,6-Hexanediol | — | 250 |
| Triethylene glycol | 2.1 | 285 |
| Glycerin | 38.8 | 290 |
| 1,2,4-Butanetriol | 4.8 | 190/18 mm |
| | 100.00 | |

The differences in volatility of propylene glycol compared to 2,3-butanediol or 1,2-butanediol are very small. As shown in Tables 2 and 3, the number of plates required to achieve 99% purity is very large, requiring the use of very tall distillation columns (55 plates or trays for 2,3-butanediol and 88 trays for 1,2-butanediol) and high energy inputs. The distillation columns required are so tall as to be impractical and very expensive. The present disclosure obviates the need for a distillation column, the heat energy needed to vaporize and separate the product mixture by distillation, and the vacuum pumps needed for distillation.

TABLE 2

Theoretical and Actual Plates Required vs. Relative volatility for Separation of Propylene Glycol and 2,3-Butanediol.

| Relative Volatility | Theoretical Plates | Actual Plates, 75% Efficiency |
|---|---|---|
| 1.25 | 41 | 55 |
| 1.35 | 31 | 42 |
| 1.45 | 25 | 34 |
| 1.50 | 23 | 31 |
| 1.70 | 18 | 24 |

TABLE 3

Theoretical and Actual Plates Required vs. Relative volatility for Separation of Propylene Glycol and 1,2-Butanediol.

| Relative Volatility | Theoretical Plates | Actual Plates, 75% Efficiency |
|---|---|---|
| 1.15 | 66 | 88 |
| 1.5 | 23 | 31 |
| 2.0 | 14 | 19 |
| 3.0 | 9 | 12 |
| 3.5 | 8 | 11 |

Several reports in the literature describe efforts for azeotropically separating glycerol derivatives such as 2,3-butanediol from propylene glycol. For instance, U.S. Pat. No. 4,935,102, incorporated herein by reference, describes a method for using an azeotrope forming agent such as propylene glycol isobutyl ether, tetrahydrofurfuryl alcohol, N,N-dimethylacetamide, ethylene glycol diethyl ether, diethylene glycol diethyl ether, 2-methoxyethyl ether, ethylene glycol n-butyl ether, diacetone alcohol and ethyl n-butyl ketone. In U.S. Pat.

No. 5,423,955, incorporated herein by reference, the azeotrope forming agent consists of a material selected from the group consisting of toluene, ethyl benzene, o-xylene, p-xylene, cumene, m-diisopropyl benzene, m-diethyl benzene, mesitylene, pcymene, hexane, cyclohexane, methyl cyclohexane, heptane, 3-methyl pentane, octane, decane, 2,3,4-trimethyl pentane, dipentene, decalin, dicyclopentadiene, alpha-phellandrene, limonene, hemimellitene, myrcene, terpinolene, p-menthol, 5-diene, beta-pinene, 3-carene, I-heptene, cyclopentane, pentane, o-diethyl benzene, 2,2-dimethyl butane and 2-methyl butane. The azeotrope forming agents described in U.S. Pat. Nos. 4,935,102 and 5,423,955 may be characterized by their Hansen solubility parameters (Table 4).

TABLE 4

Azeotropic agents used for separation of 2,3-butanediol from propylene glycol (U.S. Pat. No. 4,935,102).

| Azeotropic agent | Hansen p | Hansen h |
|---|---|---|
| Propylene glycol isobutyl ether | 5.42 | 12.52 |
| Tetrahydrofurfuryl alcohol | 10.46 | 10.96 |
| N,N-dimethylacetamide | 11.47 | 10.23 |
| Toluene | 0.75 | 1.98 |
| Ethyl benzene | 0.65 | 1.85 |
| p-Xylene | 0.91 | 1.84 |
| m-Xylene | 0.91 | 1.84 |
| o-Xylene | 0.91 | 1.84 |
| Cumene | 0.58 | 1.74 |
| Mesitylene | 0.98 | 1.7 |
| Ethylene glycol diethyl ether | 9.19 | 14.3 |
| Diethylene glycol diethyl ether | 9.22 | 12.33 |
| 2-Methoxyethyl ether | 1.81 | 7.41 |
| Ethylene glycol-n-butyl ether | 5.13 | 12.27 |
| Diacetone alcohol | 8.17 | 10.76 |
| 3-heptanone | 5.28 | 3.93 |

Azeotropic distillation using organic solvents as an agent has also proven useful for azeotropically separating ethylene glycol from 1,2-butanediol (Table 5).

TABLE 5

Azeotropic agents used for separation of 1,2-butanediol from Ethylene glycol (U.S. Pat. No. 5,432,955).

| Azeotropic agent | Hansen p | Hansen h |
|---|---|---|
| 3-Heptanone | 5.28 | 3.93 |
| Cyclohexanone | 3.13 | 5.08 |
| Diisobutyl ketone | 4.9 | 3.79 |
| Methyl isoamyl ketone | 6.03 | 4.2 |
| Isobutyl heptyl ketone | 3.76 | 3.31 |
| 2-Methoxyethyl ether | 1.81 | 7.41 |
| 2,6-Dimethyl-4-heptanone | 4.90 | 3.79 |
| p-Xylene | 0.91 | 1.84 |
| m-Xylene | 0.91 | 1.84 |
| o-Xylene | 0.91 | 1.84 |
| Ethyl benzene | 0.65 | 1.85 |
| Cumene | 0.58 | 1.74 |
| Mesitylene | 0.98 | 1.7 |

In addition, U.S. Pat. No. 5,423,955 teaches methods to remove 1,2-butanediol from propylene glycol. The following article: *Chemie Ingenieur Technik* 61(3):252-3 (1989) refers to a reverse osmosis based method for removing 2,3-Butanediol from fermentation broths. In addition *Surface Science* 559(2-3):179-185 (2004) describe adsorption of 2,3-butanediol on Si. Khanna et al in Indian patent IN 190544 describe a process for the recovery of 2,3-butanediol from fermentation broth by treating the fermentation broth containing 2,3-butanediol with a mixture of barium hydroxide and zinc sulfate and subjecting the broth to solvent extraction using an organic solvent in a feed ratio of 3:1 at a temperature in the range of 30 to 40° C. to obtain 2,3-butanediol.

The azeotropic agents used in U.S. Pat. Nos. 4,935,102 and 5,432,955 can be described by Hansen solubility parameters, which are described in detail in "Hansen Solubility Parameters: A User's Handbook," by Charles M. Hansen (CRC Press, 1999), which is incorporated by reference in its entirety. Hansen solubility parameters can be calculated using the program "Molecular Modeling Pro Plus (version 6.0.6, Norgwyn Montgomery Software, North Wales, Pa.) based on values published in the "Handbook of Solubility Parameters and Other Parameters" by Allen F. M. Barton (CRC Press, 1983) for solvents obtained experimentally by Hansen. The Hansen "h" (hydrogen bonding) values and Hansen "p" (polarity) values at 25° C. listed in Tables 4 and 5 were calculated in this manner. However, the use of azeotropic agents produces product streams which are contaminated with the azeotrope agent, necessitating additional separation steps and introducing cost into the process. The present disclosure obviates the need for azeotropic agents, distillation columns, high temperatures and vacuum pumps yet provides streams enriched in propylene glycol and depleted of unwanted butanediol compounds.

SUMMARY OF THE INVENTION

The present invention provides a method of separating at least one butanediol compound from a mixture of polyhydric alcohols containing at least one butanediol compound and at least one non-butanediol compound, comprising contacting the mixture with a chromatographic matrix. The butanediol compound or the non-butanediol compound, but not both, adsorbs to the chromatographic matrix.

The present invention further provides a method of producing a mixture of polyhydric alcohols substantially free of butanediol compounds from a mixture comprising polyhydric alcohols and at least one butanediol compound, comprising subjecting the mixture to simulated moving bed chromatography, wherein the extract comprises the mixture of polyhydric alcohols substantially free of butanediol compounds and the raffinate comprises at least one butanediol compound.

The present invention additionally provides a simulated moving bed apparatus comprising extract and raffinate, wherein the extract comprises propylene glycol substantially free of butanediol and the raffinate comprises at least one butanediol compound.

BRIEF DESCRIPTION OF THE DRAWINGS/FIGURES

FIGS. 9 and 10 are plots illustrating the results of the experiments described in Example 6.

DETAILED DESCRIPTION OF THE EMBODIMENTS

Definitions

Figure 1:
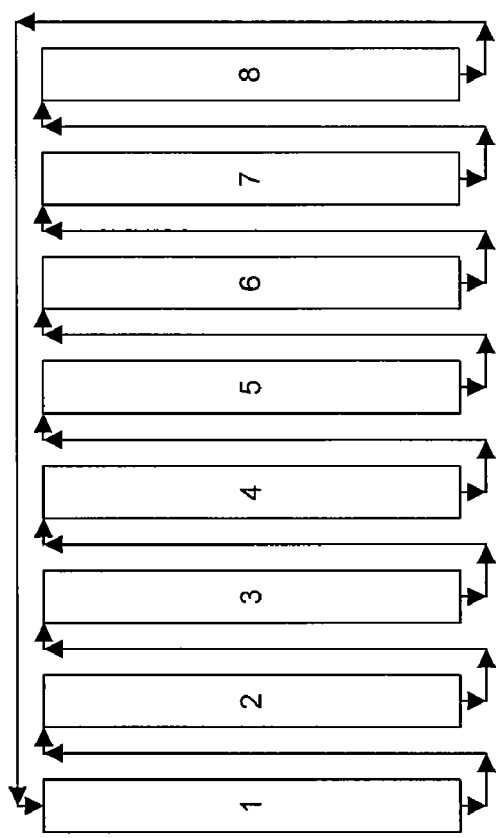
FIG. 1 is a schematic example of a simulated moving bed apparatus with eight cells or columns for use in the methods of the present invention. The exit from each cell enters the top of the next cell and all the cells are linked in this manner into a loop.

As used herein, the term "bio-derived" means derived from or synthesized by a renewable biological feedstock, such as, for example, an agricultural, forestry, plant, bacterial, or animal feedstock.

As used herein, the term "bio-based" means a product that includes in whole or in significant part, biological products or renewable agricultural materials (including, but not limited to, plant, animal and marine materials) or forestry materials.

As used herein, the term "petroleum derived" means a product derived from or synthesized from petroleum or a petrochemical feedstock.

A "butanediol compound," as the term is used herein, is any alcohol derivative of the alkane, butane, which contains two hydroxyl groups. Example compounds include, but are not limited to, 1,4-butanediol, 1,2butanediol and 2,3-butanediol. In some embodiments, butanediol compounds are 1,2-butanediol and 2,3-butanediol.

As used herein, the term "polyhydric alcohols," also sometimes referred to as sugar alcohols, polyalcohols or polyols, refers to compounds containing more than one hydroxyl functional group, including hydrogenated forms of carbohydrates whose carboxyl group (=O) in functional groups such as an aldehyde or ketone, has been reduced to a primary or secondary hydroxyl group.

As the term is used herein, "matrix" (also known as "chromatographic matrix" or "adsorptive matrix") includes any solid substance capable of adsorbing a contaminant and includes but is not limited to carbon, charcoal (activated or non-activated), bentonite, smectite clay, montmorillonite clay, diatomaceous earth, or any other suitable adsorbent material and mixtures thereof. Chromatographic matrices suitable for the methods of the present invention may be acid or base washed with or without subsequent neutralization and may comprise any physical form that accomplishes the purposes of the present invention.

The term "carbon" as used herein includes solid forms of carbon and includes charcoal, both activated and non-activated.

As used herein, the term "charcoal" includes forms of carbon obtained by the partial oxidation of organic material, particularly by the burning of wood, coal, lignin, bone or other organic matter in a reducing atmosphere.

The term "bentonite clay," as used herein, is an absorbent aluminum phyllosilicate clay that is generally impure and consists mostly of montmorillonite.

The term "montmorillonite," as used herein, refers to a soft phyllosilicate mineral that typically forms in microscopic crystals, forming a clay. Montmorillonite is the main constituent of the volcanic ash weathering product, bentonite. The water content of Montmorillonite is variable and Montmorillonite increases greatly in volume when it absorbs water. Chemically, it is hydrated sodium calcium aluminum magnesium silicate hydroxide. Potassium, iron, and other cations are common substitutes; the exact ratio of cations varies with source. Montmorillonite can be intermixed with chlorite, muscovite, illite, cookeite and kaolinite.

As used herein, the term "adsorption" refers to a process that occurs when a gas or liquid solute accumulates on the surface of a solid or, more rarely, a liquid (adsorbent), forming a molecular or atomic film (the adsorbate). Adsorption is different from absorption, in which a substance diffuses into a liquid or solid to form a solution. The term sorption encompasses both processes, while desorption is the reverse process. Adsorption is operative in most natural physical, biological, and chemical processes, and is widely used in industrial applications such as activated charcoal, synthetic resins and water purification. Adsorption, ion exchange and chromatography are sorption processes in which certain adsorptive compounds are selectively transferred from the fluid phase to the surface of insoluble, rigid particles suspended in a vessel or packed in a column. As used herein, the term "adsorb" generally refers to the process where a material adsorbs to the surface of the chromatographic matrix. However, the adsorbing material may also be absorbed into the chromatographic process. In other words, the term "adsorb," as used herein, refers to the process of adsorption, but when a material adsorbs to the chromatographic matrix, absorption may also occur, i.e., both processes may take place.

The process of "contacting the solvent mixture with a chromatographic matrix," as that phrase is used herein, refers to, for example, flowing a liquid solvent mixture over the solid chromatographic matrix. Another example refers to allowing a liquid solvent mixture to incubate with the solid chromatographic matrix in a non-flowing condition. In some embodiments, the solvent mixture flows over the stationary chromatographic matrix wherein the matrix is divided into zones.

The term "non-functional resin" (also known in the industry as non-ionic resin) as used herein refers to synthetic materials, typically spherical, having a chemical structure based on a cross-linked three-dimensional polymer molecule, typically styrene and di-vinyl benzene (DVB).

As used herein, the term "macroporous resin" refers to an inert material that is able to adsorb butanediols in preference to other polyhydric alcohols. Such resins typically have a pore diameter range of 46-700 angstroms, and the specific volume of the pores ranges from 0.5-2.1 cc/g in our results.

As the term is used herein, "molecular sieve" refers to a material containing small pores of a precise and uniform size that is used as an adsorbent for gases and liquids. In molecular sieves, molecules small enough to pass through the pores are adsorbed while larger molecules are not. Molecular sieves are different from a common filter in that they operate on a molecular level. For instance, a water molecule may be small enough to enter the molecular sieves while larger molecules are not. Because of this, they often function as a desiccant. A molecular sieve can adsorb water up to 22% of its own weight. Often molecular sieves consist of aluminosilicate minerals, clays, porous glasses, charcoals, zeolites, active carbons, or synthetic compounds that have open structures through which small molecules, such as nitrogen and water can diffuse.

As the term is used herein, "simulated moving bed chromatography" ("SMB") is a chromatographic technique that is based on the principle that a flow of liquid (mobile phase) moving countercurrent to a constant flow of solid (stationary phase) enhances the potential for the separation and, hence, makes the process more efficient. SMB also allows a continuous flow of feed material to be separated, which improves the throughput of the equipment compared to traditional batch chromatography and greatly simplifies handling of feed, products, and co-products. Providing a constant flow of solid is impractical in a production process. Therefore, in simulated moving bed chromatography, the solid instead is packed into columns. In some embodiments, these columns are arranged in a carousel formation made up of any number of sections or zones with one or more columns per section. In some embodiments, manifolds at the top and bottoms of the carousel provide the flow of liquid from one column to the next and allow introduction of inlets and removal of outlets. For example, two inlet streams (feed and eluent) and two outlets streams (extract (product) and raffinate) can be directed in alternating order to and from the column ring. To simulate the moving of the beds, the manifolds are rotated stepwise at regular time intervals, thus moving the inlet and outlet positions and simulating countercurrent movement of columns.

As the term is used herein, "raffinate" refers to the effluent stream that is depleted of the desired component. In some embodiments, the raffinate is depleted of the propylene glycol (PG) components. In additional embodiments, the raffinate is the mixture of butanediol contaminants minus the remaining polyhydric alcohols. In some embodiments, the raffinate components are the poorly adsorbed components, relative to PG. In other embodiments, the raffinate components are the more strongly bound material, relative to PG. Typically, raffinate is contained in one of the outlet streams of the SMB apparatus. In some embodiments of the present invention, the raffinate is a mixture of some polyhydric alcohols plus the butanediol contaminants. In some embodiments, the butanediol contaminants adsorb to the chromatographic matrix.

The term "extract," also referred to as "product," as used herein, refers to the effluent stream that contains the polyhydric alcohols. In some embodiments, the extract is depleted of all components except the propylene glycol (PG) components. Typically, but not always, the extract are the unabsorbed or intermediately adsorbed components. Typically, one of the outlet streams in simulated moving bed chromatography contains extract or product.

As used herein, the term "substantially free of butanediol compounds" refers to mixture of polyhydric alcohols or a propylene glycol product that contains less than about 2% butanediols. The term also can refer to a mixture of polyhydric alcohols that is classified as a U.S.D.A. Certified Bio-based Product according to the Farm Security and Rural Investment Act of 2002, section 9002 (7 U.S.C. 8102).

As used herein, the term "elution" (or "elute"), refers to the process of extracting one material from another by washing with a solvent to remove adsorbed material from an adsorbent.

The term "eluent," as used herein, refers to a material capable of desorbing an extract component from the adsorbent.

A "feed mixture," as used herein, is a mixture containing one or more extract components and one or more raffinate components to be separated by the methods of the present invention. The term "feed stream" indicates a stream of a feed mixture which is passed into contact with the adsorbent used in the methods of the present invention.

The term "depleted of," as used herein, indicates that a given compound is reduced or diminished in concentration, number or quantity.

As the term is used herein, "ternary separation" refers to a separation of a mixture comprising at least three compounds into three streams, each of which is enriched in a different compound which can be recovered from the feed mixture. This is also called "ternary desorption". In some embodiments, using a simulated moving bed chromatography apparatus, three effluent streams may be employed. In some embodiments, one effluent stream is enriched in PG, a second effluent stream may be enriched in another component of the feed mixture, such as 2,3-butanediol. A third effluent stream may be enriched in another component of the feed mixture, such as 1,2-butanediol.

As the term is used herein, "system" refers to an apparatus comprising an SMB apparatus, together with a matrix and conduits bringing feed mixture to the apparatus and conduits bringing extracts or products from the apparatus comprise a separation system. In an embodiment, the system may be used to produce an extract or product mixture of polyhydric alcohols substantially free of butanediol compounds from a mixture comprising polyhydric alcohols and at least one butanediol compound, comprising contacting the mixture with a matrix in a simulated moving bed chromatography apparatus, wherein an extract or product stream is enriched in propylene glycol and depleted of butanediol compounds and a raffinate is depleted of propylene glycol and enriched in butanediol compounds relative to a feed stream.

Introduction

The invention pertains to the removal of butanediols, such as 1,2-butanediol ("1,2-BDO") and 2,3-butanediol ("2,3-BDO"), from a mixture of polyhydric alcohols such as ethylene glycol, propylene glycol and glycerol. In some embodiments, the mixture of polyhydric alcohols contains not only BDOs, ethylene glycol, propylene glycol and glycerol, but also lactic acid (2-hydroxypropanoic acid) and other organic acids. In some embodiments, the invention results in a propylene glycol product that is substantially free of all contaminants. In some embodiments of the present invention, the mixture of polyhydric alcohols results from the hydro cracking of carbohydrates or hydrogenolysis of alcohols. The boiling points of the polyhydric alcohols contained in the mixture are quite similar to one another, resulting in difficulties in isolating the desired product, such as propylene glycol or ethylene glycol, in a substantially purified form. Some prior methods have used azeotropic solvent mixtures for separating substantially purified propylene glycol and ethylene glycol from 1,2-butanediol and 2,3-butanediol. Suitable azeotrope forming agents are typically organic compounds and are difficult to process and handle due to environmental regulations. Azeotrope forming agents can also be expensive.

This present invention avoids the use of expensive solvents, complicated azeotropes, and complicated distillation techniques and thus presents a unique and convenient way to remove butanediol impurities from propylene glycol and ethylene glycol by using an adsorption or chromatographic technique. The invention also provides methods to obtain a propylene glycol product that is substantially free of other contaminants, i.e., contains less than 2% BDOs, ethylene glycol, glycerol and lactic acid (or other organic acids).

The present invention provides the use of adsorbents for removing 1,2-butanediol and 2,3-butanediol from a mixture of polyhydric alcohols. Typically, a mixture of propylene glycol, ethylene glycol, glycerol, low levels of butanediols, lactic acid, sodium hydroxide and other organic acids are produced from hydrogenolysis. The adsorption techniques of the present invention allow even these low levels of butanediols to be separated from other polyhydric alcohols.

Methods of Separating Butanediol Compounds from Mixtures of Polyhydric Alcohols

The present invention provides methods of separating at least one butanediol compound from a mixture of polyhydric alcohols containing at least one butanediol compound and at least one non-butanediol compound. In some embodiments, such methods comprise contacting the mixture with a chromatographic or adsorptive matrix, wherein at least one butanediol compound or at least one non-butanediol compound preferentially adsorbs to the chromatographic matrix, compared to the other components of the mixture. Thus, the methods of the present invention include methods where the butanediol compounds preferentially adsorb to the chromatographic, or adsorptive matrix, or the polyhydric alcohols such as propylene glycol or ethylene glycol preferentially adsorb to the chromatographic matrix.

If desired, the butanediol compounds that adsorb to the matrix can be eluted and recovered. Likewise, if the chromatographic matrix preferentially adsorbs polyhydric alcohols other than butanediol compounds, the polyhydric alcohols that adsorb to the matrix can be eluted and recovered. In some embodiments, the material that preferentially adsorbs to the matrix elutes from the matrix without the need for an additional eluent. For example, in some embodiments a mixture of propylene glycol, ethylene glycol, glycerol, BDOs, and organic acids are contacted with the chromatographic matrix. The least adsorbed component elutes from the matrix first and the most adsorbed component elutes from the component last, with the intermediately adsorbed components eluting in between the first and the last components.

In other embodiments, the butanediol component, for example, adsorbs to the chromatographic matrix and elutes from the matrix upon feeding an eluent, such as a primary alcohol, into the SMB apparatus.

In some embodiments, one of the polyhydric alcohol components, such as propylene glycol, adsorbs to the matrix and is eluted from the matrix.

In certain some embodiments the product comprises a stream that is enriched in propylene glycol and is and depleted of other polyhydric alcohols. In this embodiment, the propylene glycol component is poorly adsorbed to the matrix. Two raffinate discharges are therefore released from the SMB apparatus, one enriched in polyhydric alcohols and one enriched in BDO components. In some embodiments, the raffinate discharge enriched in polyhydric alcohols is eluted from the SMB apparatus with deionized water and the raffinate discharge stream that is enriched in BDO components is eluted using methanol.

In some embodiments, at least one butanediol compound adsorbs to the chromatographic matrix and the mixture of polyhydric alcohols comprises propylene glycol, ethylene glycol or a mixture thereof. In some embodiments, at least one butanediol compound is 1,2-butanediol, 2,3-butanediol, or a mixture thereof. Suitable chromato-graphic matrices for butanediol adsorption include those that adsorb butanediol compounds by covalent, ionic, hydrogen or any other polarity based binding.

In some embodiments, the chromatographic, or adsorptive, matrix comprises a material that selectively adsorbs at least one butanediol compound over the remaining components of the mixture of polyhydric alcohols. Such matrices include, but are not limited to, carbon black, carbon powder, activated charcoal, non-activated charcoal, diatomaceous earth, silica, alumina, clay, and resin. In some embodiments, the chromatographic matrix is a carbon powder.

In further embodiments, the chromatographic, or adsorptive, matrix is alumina. For example, the alumina is neutral alumina, basic alumina and acidic alumina. The present invention also provides chromatographic matrices comprising clay. Examples of clays suitable for use in the present invention include, but are not limited to, bentonite clay, smectite clay and montmorillonite clay. In additional embodiments, the chromatographic matrix is a resin material, such as an ion exchange resin.

In some embodiments, the ion exchange resin is selected from the group consisting of a weak acid cation exchange resin, a strong acid cation exchange resin, a weak base anion exchange resin and a strong base anion exchange resin. In further embodiments, the resin is a carbon-based macroporous resin. Such carbon-based macroporous resin includes, but is not limited to Lewatit AF-5. In further embodiments, the chromatographic matrix is a non-ionic resin. Non-ionic resins are also referred to as non-functional resins. Such resins can be, but are not limited to, Lewatit S7768, Lewatit VP OC 1064, Mitsubishi SP70, Mitsubishi SP700, Mitsubishi HP21, Mitsubishi SP207, Mitsubishi SP825, Mitsubishi SP825L, Mitsubishi SP850, Dow V493, Dow SD-2, Finex FAD70, Finex FAD118, Purolite MN200, Rohm & Haas XAD4, and Rohm & Haas XPF66.

In additional embodiments, the chromatographic, or adsorptive, matrix is a molecular sieve. Suitable molecular sieves include, but are not limited to, UOP Molecular Sieve from UOP (UOP LLC, Des Plaines, Ill. USA) Molecular Sieve Type 3A; (Chemical Name: Sodium/Potassium Aluminosilicate; Synonyms: Zeolite); 564ET3A and 562Et from Grace Davison (W.R. Grace & Co.-Conn., Baltimore, Md. USA) Sylobead 562Et: Sylobead 564Et: crystalline aluminosilicate; type Z Grade 3A-8 from Sphinx (Sphinx Adsorbents, Inc. Springfield Mass. USA), Type Z Molecular Sieve; and Z3-03 from Zeochem (Louisville, Ky. USA), Zeochem Z3-03, chemical name: $M_{x/n}$ $[(AlO_2)_x(SiO_2)_y]+H_2O$, chemical formula: synthetic sodium potassium or calcium aluminosilicate, chemical family: molecular sieve Zeolite.

Chromatographic, or adsorptive, matrices can be in any suitable physical form. Suitable examples include, but are not limited to, powder, pellets, granules or a combination thereof. For example, in one embodiment, activated granular carbon or bentonite having 12×40, 20×40, 30×60, 8×30 or any similar sieve size may be used. Chromatographic matrices suitable for the methods of the invention may be acid or base washed with or without subsequent neutralization. It is well known in the art that adsorptive matrices may be reused through regeneration, for example, by acidification, alkalization or change in polarity of solvent using for regeneration. As such, matrices such as carbon, for example, may be regenerated for multiple uses. Although such regenerated matrices may lose adsorptive capacity with use, such additional steps of regeneration are encompassed by the present invention.

The present invention further provides a method of producing a mixture of polyhydric alcohols substantially free of butanediol compounds from a mixture comprising polyhydric alcohols and at least one butanediol compound. In some embodiments of the present invention, the mixture of polyhydric alcohols results from the catalytic hydrogenolysis of glycerol. Catalytic hydrogenolysis, also referred to as hydrocracking, is a process whereby a polyol, such as a sugar, glycerol or glycols are reacted with hydrogen to produce other polyols. The polyols produced from this process often comprise a mixture of polyols having a lower average molecular weight than the starting material.

The mixture of polyols produced from catalytic hydrogenolysis provide a suitable material for the methods of the present invention. In some embodiments, the mixture of polyhydric alcohols results from the catalytic hydrogenolysis of glycerol. In some embodiments of the present invention, the glycerol, in turn, is a byproduct from the production of biodiesel via a transesterification reaction between an oil, such as a vegetable oil, and an alcohol.

The catalytic hydrogenolysis of polyols produces not only desired components, such as propylene glycol and ethylene glycol, but also can produce several unwanted products, such as 1,2-butanediol, 1,3-butanediol, 1,4-butanediol and 2,3-butanediol. In some embodiments of the present invention, the reaction product of the catalytic hydrogenolysis of a polyol, such as glycerol, produces a mixture of polyhydric alcohols that contain from about 0.1% to about 13% by volume butanediol contaminants.

In some embodiments, the mixture of polyhydric alcohols is subjected to simulated moving bed chromatography, wherein the extract, or product comprises the mixture of polyhydric alcohols substantially free of butanediol compounds and the raffinate comprises at least one butanediol compound. In this embodiment of the present invention, the raffinate, i.e., the component of the mixture that does not preferentially adsorb to the chromatographic matrix, is the mixture of polyhydric alcohols substantially free of the butanediol contaminants discussed above. The extract, by contrast, is the component of the mixture that preferentially adsorbs to the chromatographic matrix. In some embodiments, the raffinate is substantially free of butanediol compounds, meaning that the raffinate contains less than about 2% butanediol compounds. The term "substantially free of butanediol components" also can refer to a mixture of polyhydric alcohols that is classified as a U.S.D.A. Certified Biobased Product according to the Farm Security and Rural Investment Act of 2002, section 9002 (7 U.S.C. 8102).

The present invention additionally provides a method of operating a simulated moving bed apparatus so that a ternary separation is achieved. In some embodiments, a ternary separation can be achieved. In an embodiment, a feed mixture comprising PG and one or more butanediol, such as 1,2-BDO and 2,3-BDO, can be separated into an effluent enriched in PG, an effluent enriched in 1,2-BDO, and an effluent enriched in 2,3-BDO.

Most simulated moving bed ("SMB") adsorptive separation units simulate countercurrent movement of the adsorbent and the feed stream using established commercial technology. The adsorbent is loaded into several columns (cylindrical adsorbent chambers), often arranged in a ring and mounted in a carousel for convenience. Each column is connected to the two adjacent columns to allow the flow of liquids between columns. In some equipment, manifolds are positioned at the top and bottoms of the columns, and by shifting the manifolds stepwise with respect to the beds, the movement of the bed is simulated. The positions at which the streams involved in the process enter and leave the columns are shifted so that they enter or leave different beds. In some embodiments of the present invention, the SMB unit has at least four streams (feed, eluent, extract and raffinate) employed in this procedure and the location at which the feed and desorbent streams enter the chamber and the extract and raffinate streams leave the chamber are simultaneously shifted in the same direction at set intervals. Each shift in the location of these transfer points delivers or removes liquid from a different sub-bed of adsorbent within the chamber. Thus, each column passes through all of the zones of the apparatus during each complete revolution of the manifolds with respect to the beds.

These processes typically include at least three or four separate steps which are performed sequentially in separate zones within a mass of adsorbent or matrix retained in one or more vertical cylindrical adsorption chambers (columns). Each of these zones normally is formed from a plurality of beds of adsorbent, sometimes referred to as sub-beds, with the number of beds per zone ranging from 1 or 2 up to 8-12. All of the beds are contained in one or more vertical vessels referred to herein collectively as the adsorbent chamber. The beds are structurally separated from one another by a horizontal liquid collection/distribution grid. Each grid is connected to a transfer line defining a transfer point at which process streams such as the raffinate and extract stream enter and leave the vertical adsorption chambers.

The general technique employed in the performance of a simulated moving bed adsorptive separation is described in the literature. Numerous other available references describe many of the mechanical parts of a simulated moving bed apparatus and procedure, including rotary valves for distributing various liquid flows to the bed lines, the internals of the adsorbent chambers and control procedures.

Countercurrent simulated moving bed processes and equipment are described in many available references, such as U.S. Pat. No. 2,985,589, incorporated herein by reference for its teaching of the practice of simulated moving bed adsorptive separation processes. Cyclic advancement of the input and output streams of this simulation can be accomplished by a manifolding setup or by rotary disc valves as shown in U.S. Pat. Nos. 3,040,777 and 3,422,848. Equipment using these principles can vary in size from the pilot plant scale shown in U.S. Pat. No. 3,706,812 to commercial petrochemical plant scale, with flow rates ranging from a few cc per hour to many thousands of gallons per hour.

Large scale plants normally employ rotary valves having a port for each transfer line while small scale and high pressure units tend to use valves having only two or three ports. The invention may also be practiced in a concurrent continuous process, like that disclosed in U.S. Pat. Nos. 4,402,832 and 4,478,721. The functions and properties of adsorbents and desorbents in the chromatographic separation of liquid components are well-known, and reference may be made to U.S. Pat. No. 4,642,397, which is incorporated herein, for additional description of these adsorption fundamentals.

During the adsorption step of the process a feed mixture containing a mixture of compounds is contacted with the adsorbent at adsorption conditions and one compound(s) or class of compounds is selectively adsorbed and retained by the adsorbent while the other compounds of the feed mixture are relatively unabsorbed. When the adsorbent contains a near equilibrium loading of the more selectively adsorbed compound, it is referred to as a "rich" adsorbent. In the next step of the process, the unabsorbed (raffinate) components of the feed mixture are then removed from the interstitial void spaces between the particles of adsorbent and from the surface of the adsorbent. This depleted liquid and any eluent which becomes admixed with it during passage through the adsorption zone in this step is removed from the process as a process stream referred to as the raffinate stream. The adsorbed compound is then recovered from the rich adsorbent by contacting the rich adsorbent with a stream comprising the eluent at desorption conditions in a desorption step. The eluent displaces a stream that is enriched in the desired compound to form an extract stream, which, in some embodiments, is transferred to a separation means for recovery of the desired compound from the extract stream containing a mixture of the desired compound and eluent.

In some embodiments, all or a part of the extract stream or all or a part of the raffinate stream, or both, are passed to separation means, typically fractional distillation columns, to recover at least a portion of the eluent and a portion of the extract or the raffinate, or both. What is produced from the separation means is therefore an extract product, where the extract component is present in a higher concentration in the extract product than found in the extract stream. Likewise, the raffinate product produced after the separation process contains a higher percentage of raffinate components than found in the raffinate stream.

Thus, in another aspect of the invention, adsorbed butanediols are recovered from the adsorbent using an eluting solvent such as a primary alcohol that will allow recovery of substantially pure butanediols after distillation of the primary alcohol. In an additional embodiment, the material containing butanediols is transported or shipped (i.e., distributed) to another location for subsequent incorporation into a composition. The container or the composition may also be associated with indicia indicating that the material contains less than a specified amount of the butanediols.

Suitable eluting solvents, also referred to as eluents, for use in the present invention include, but are not limited to water, such as deionized water, and primary alcohols, such as methanol and ethanol. Additional suitable eluents can be used and techniques to determine such eluents are known to those of skill in the art.

An explanation of simulated moving bed processes is given in the Adsorptive Separation section of the Kirk-Othmer Encyclopedia of Chemical Technology; the pages relating to SMB chromatography are incorporated herein by reference.

In some embodiments of the present invention, the mixture of polyhydric alcohols is contacted with a chromatographic matrix. Contacting the mixture of polyhydric alcohols with the chromatographic matrix comprises flowing the mixture of polyhydric alcohols over or through the chromatographic matrix. Thus, when a simulated moving bed unit is used to separate the butanediol compounds from the remaining polyhydric alcohols, the feed stream containing all components is fed into the SMB apparatus.

In some embodiments of the present invention, the product, or extract comprises a mixture of polyhydric alcohols, which include propylene glycol. Thus, the raffinate comprises butanediol compounds. The product comprising the mixture of polyhydric alcohols is then subjected to further separation steps to recover substantially purified propylene glycol.

Simulated Moving Bed Apparatus for Separation of Butanediols from Mixtures of Polyhydric Alcohols The present invention also provides a simulated moving bed apparatus comprising raffinate and extract, wherein the product comprises propylene glycol substantially free of butanediol and the raffinate comprises at least one butanediol compound. In another embodiment, the present invention also provides a simulated moving bed apparatus comprising raffinate, product PG, and recycled raffinate wherein the product comprises propylene glycol substantially free of butanediol, the raffinate comprises 2,3-butanediol, and the recycled raffinate comprises 1,2-butanediol. In another embodiment, the present invention also provides a simulated moving bed apparatus comprising raffinate 1, raffinate 2, and product PG wherein the product PG comprises propylene glycol substantially free of butanediol, the raffinate 1 comprises butanediols, and the raffinate 2 comprises 1,2-butanediol.

Figure 11:
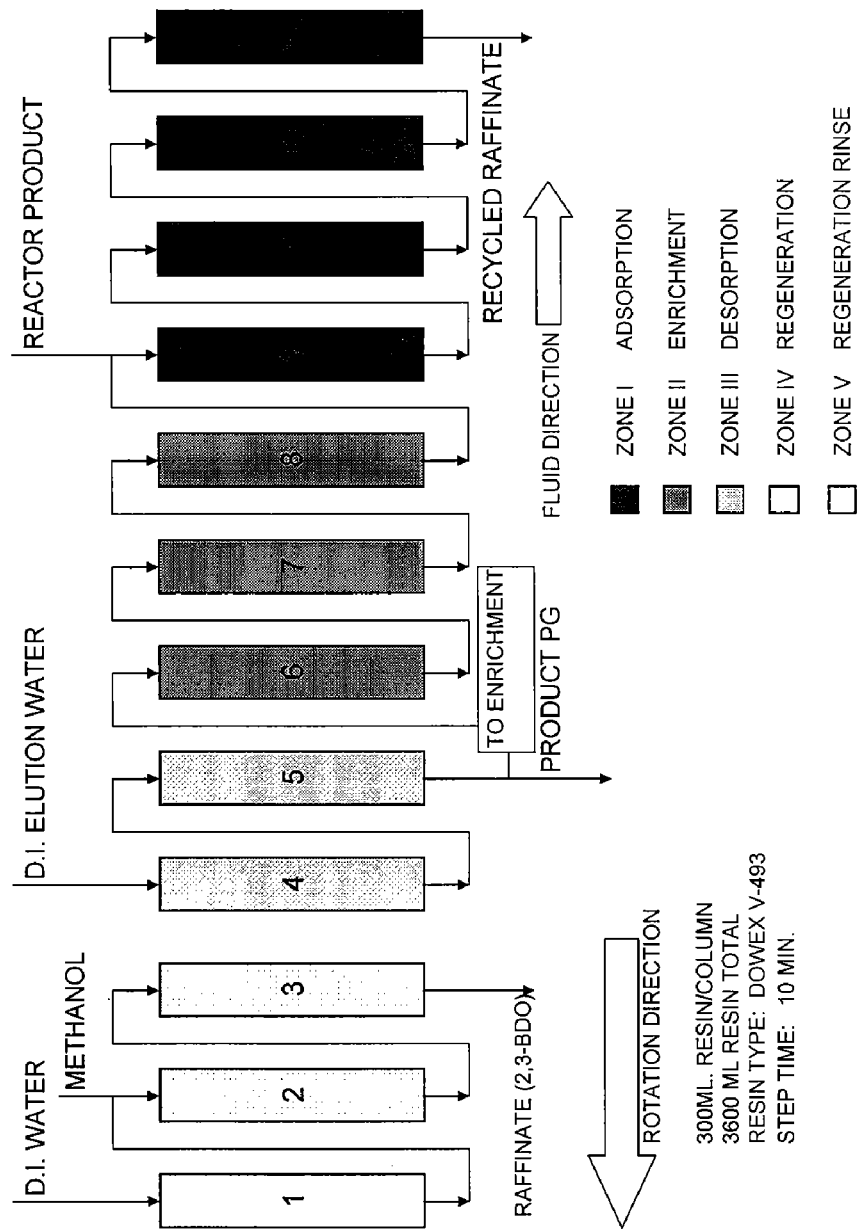
FIG. 11 is a diagram illustrating the simulated moving bed chromatography apparatus configured in the 1-2-2-3-4 sequence described in Example 7.
Figure 12:
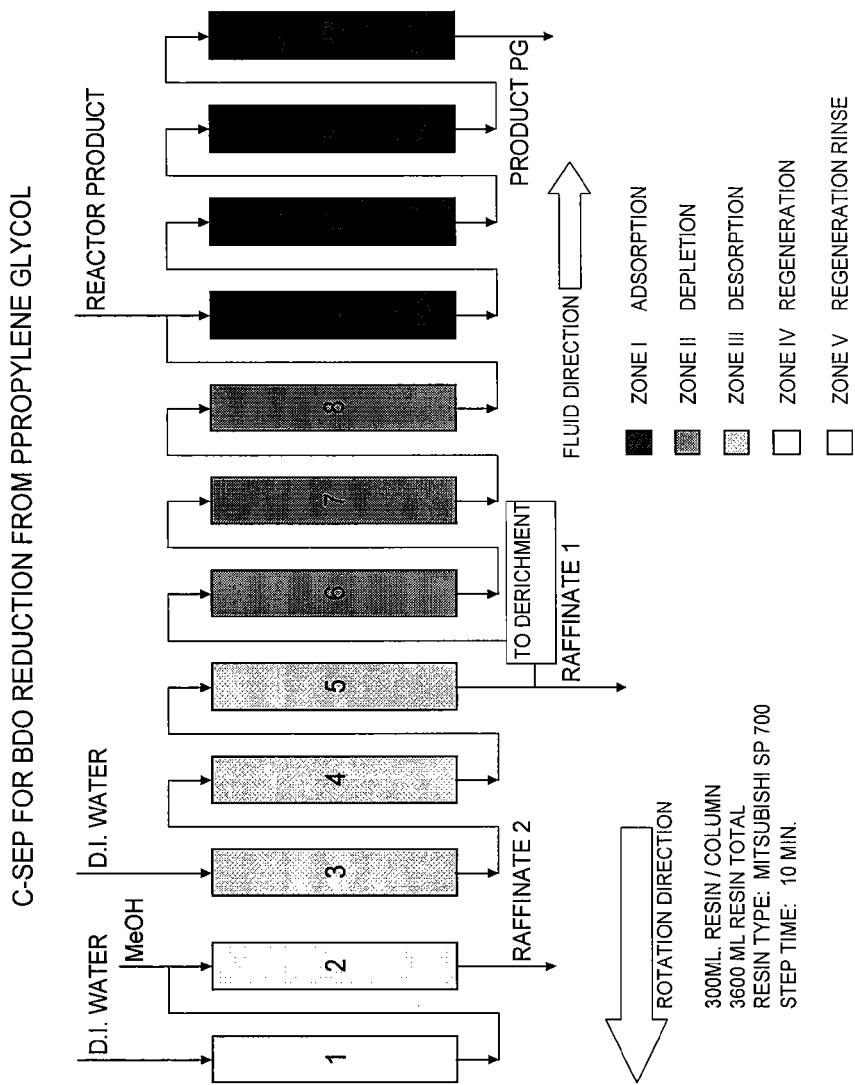
FIG. 12 is a diagram illustrating the simulated moving bed chromatography apparatus configured in the 1-1-3-3-4 sequence described in Example 8.

FIG. 1 is a simplified schematic of an SMB apparatus. In an SMB apparatus, the exit from each cell enters the top of the next cell. FIGS. 11 and 12 illustrate examples of a simulated moving bed apparatus for use in the methods of the present invention. The SMB apparatus is drawn schematically using a set of cells or columns. The exit from each cell enters the top of the next cell and all the cells are linked in this manner into a loop. A typical SMB apparatus contains four valves: a feed valve, an eluent valve, an extract valve and a raffinate valve. In a ternary separation, i.e., a separation of a mixture containing at least three compounds into at least three streams, each enriched in a different compound, the SMB apparatus contains an additional valve to remove the third stream. The third stream may be an additional extract stream or may be an additional raffinate stream. To simulate true moving bed chromatography, the valves are switched periodically, such that, for example, the feed valve is switched in the same direction as the liquid flow. The other three (or four) valves, eluent, extract and raffinate, must also move in this manner.

The SMB apparatus also optionally comprise a temperature-control device that keeps the temperature of the apparatus from about 30° C. to 70° C.

In some embodiments of the present invention, the flow rate of the feed into the SMB apparatus is from about 3 to 98 gallons per minute ("GPM"), in some embodiments from about 20-40 GPM, and in other embodiments, about 30 GPM.

In some embodiments of the present invention, the flow of the enrichment zone (i.e, the zone bracketed by extract or product discharge port and the feed inlet port) is from about 29 GPM to about 313 GPM, in some embodiments from about 50 to 70 GPM, and in further embodiments, about 60 GPM.

In some embodiments of the present invention, the eluent flow is from about 38 GPM to 546 GPM, in some embodiments from about 55 GPM to about 85 GPM, and in further embodiments, about 75 GPM.

In some embodiments of the present invention, the rinse flow, e.g., methanol flow, to remove any adsorbed compounds is from about 28 GPM to about 313 GPM, in some embodiments from about 90 GPM to about 100 GPM, and in further embodiments, about 97 GPM.

EXAMPLES

Materials and Methods

A preliminary test, called "pulse test," may be employed to test adsorbents and determine optimal conditions for simulated moving bed chromatography. In a pulse test, a particular feed mixture and desorbent material are examined to measure adsorbent characteristics such as adsorptive capacity, selectivity, resolution and exchange rate. The basic pulse test apparatus consists of a tubular adsorbent chamber (e.g. a glass column) containing adsorbent and having an inlet and outlet at opposite ends of the chamber. The column is jacketed for temperature control. Quantitative and qualitative analytical equipment such as refractometers, polarimeters and chromatographs can be attached to an outlet line of the chamber and used to detect quantitatively and/or determine qualitatively one or more components in the effluent stream leaving the adsorbent chamber.

During a pulse test, the adsorbent is first filled to equilibrium with a particular eluent by passing the eluent through the adsorbent chamber. A pulse of the feed mixture, sometimes diluted in desorbent, is then injected or applied to the top of the adsorbent bed. Eluent flow is resumed, and the feed components are eluted as in a liquid-solid chromatographic operation. The effluent can be analyzed on-stream. Alternatively, or in addition effluent fractions can be collected and later analyzed separately. Traces of the envelopes of corresponding component peaks can then be plotted in terms of component concentration versus quantity of effluent.

From information derived from the pulse test the adsorbent/eluent performance can normally be rated in terms of retention volume for an extract or a raffinate component, selectivity for one component with respect to the other, stage time, the resolution between the components and the rate of desorption of an extract component by the eluent. The retention volume of an extract or a raffinate component may be determined from the distance between the center of the peak envelope of an extract or a raffinate component and the peak envelope of a tracer component or some other known reference point. It is expressed in terms of the volume in cubic centimeters of eluent pumped during the time interval corresponding to the distance between the peak envelopes.

Example 1

PG reactor product was prepared by hydrogenolysis of a 40% solution of glycerol containing sodium hydroxide in a 2000 ml high-pressure Stainless Steel 316 reactor as described in U.S. patent application 60/913,572, filed Apr. 24, 2007. Solid catalyst was loaded in the reactor to a final volume of 1000 ml of catalyst. The reactor was jacketed with a hot oil bath to provide for the elevated temperature for reactions and the feed and hydrogen lines were also preheated to the reactor temperature. A solution of a 40% solution of glycerol containing sodium hydroxide was fed through the catalyst bed at LHSV ranging from 0.5 hr-1 to 2.5 hr-1. Hydrogen was supplied at 1200-1600 psi and was also re-circulated through the reactor at a hydrogen to glycerol feed molar ratio of from 1.4:1 to 1.6:1. Between 47.7-96.4% of the glycerol was converted to polyhydric alcohols and between 36.3-55.4% of propylene glycol was produced. In addition to propylene glycol, the hydrogenolysis reaction produced 0.04-2.31% unwanted BDO, which present a problem for recovery of pure propylene glycol.

Figure 2:
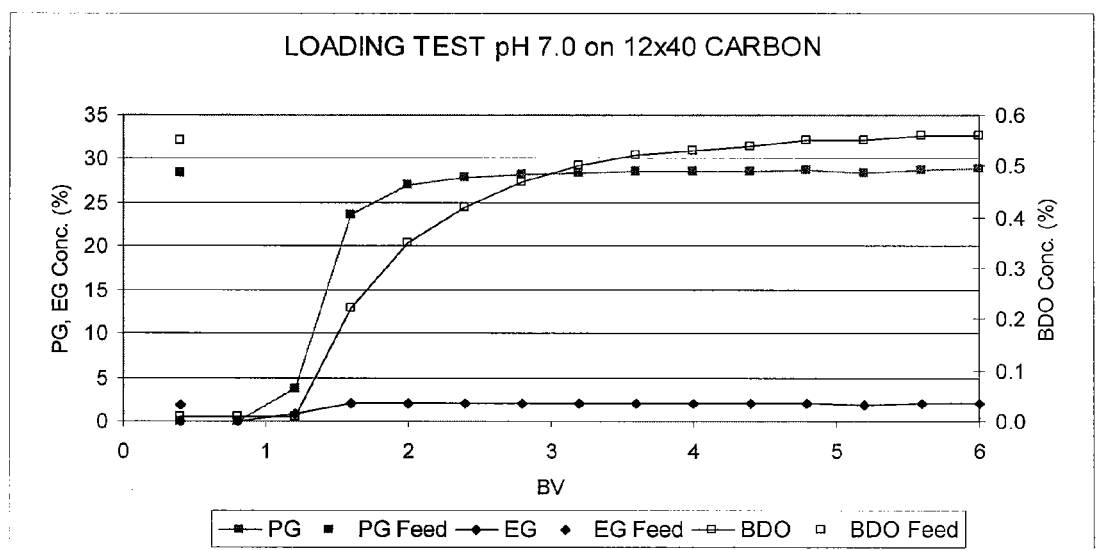
FIGS. 2 and 3 are plots illustrating the results of the experiments described in Example 1.
Figure 3:
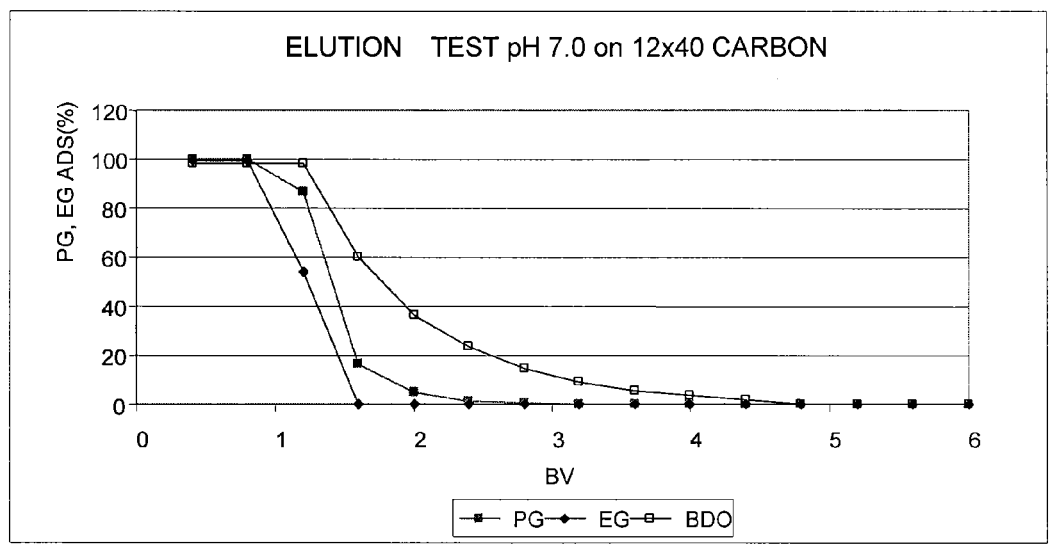

600 ml of a feed ("PG reactor product") containing 28.30% 1,2-propanediol and 0.55% 2,3-butanediol was contacted with a Calgon CPG 12×40 granular carbon bed containing 100 ml of packed carbon in a glass column. Temperature of 70 degrees C. and flow rate of 5 ml/min was used. The results are shown in table below and show the 2,3-BDO may be separated from other polyhydric alcohols by using a carbon bed. The results of this example are also shown in FIGS. 2 and 3. FIG. 2 is a plot from a breakthrough (capacity, or loading) test. In FIG. 2, the horizontal axis is the bed volume ("BV"), the left vertical axis is the concentration in percentage of propylene glycol, i.e., 1, 2-propanediol, and ethylene glycol in the column effluent. The right vertical axis is shows butanediol concentration in the column effluent. Effluent fractions enriched in PG and EG and depleted of BDO were recovered, and BDO was recovered from the carbon bed by elution with 100% ethanol (FIG. 3). FIG. 3 shows the results of this desorption (elution, or stripping) or regeneration test. In FIG. 3, the horizontal axis is the BV, and the vertical axis is the concentration, in percentage, of the propylene glycol and ethylene glycol which remained in the column bed using ethanol regeneration.

| Sample Id | Bed Volume | 1,2-Propanediol % | % Adsorbed | Ethylene Glycol % | % Adsorbed | 2,3-Butanediol % | % Adsorbed |
|---|---|---|---|---|---|---|---|
| 112206 Test 22-Feed | | 28.30 | — | 1.94 | — | 0.55 | — |
| 112206 Test 22-5 | 0.4 | 0.01 | | 0.01 | | 0.01 | |
| 112206 Test 22-10 | 0.8 | 0.01 | | 0.01 | | 0.01 | |
| 112206 Test 22-15 | 1.2 | 3.76 | | 0.89 | | 0.01 | |
| 112206 Test 22-20 | 1.6 | 23.61 | | 1.97 | 0.00 | 0.22 | |
| 112206 Test 22-25 | 2 | 26.95 | | 1.97 | 0.00 | 0.35 | |
| 112206 Test 22-30 | 2.4 | 27.93 | | 1.97 | 0.00 | 0.42 | |
| 10106 Test 16-35 | 2.8 | 28.21 | | 1.96 | 0.00 | 0.47 | |
| 112206 Test 22-40 | 3.2 | 28.38 | 0.00 | 1.96 | 0.00 | 0.50 | |
| 112206 Test 22-45 | 3.6 | 28.54 | 0.00 | 1.97 | 0.00 | 0.52 | |
| 112206 Test 22-50 | 4 | 28.58 | 0.00 | 1.96 | 0.00 | 0.53 | |
| 112206 Test 22-55 | 4.4 | 28.61 | 0.00 | 1.96 | 0.00 | 0.54 | |
| 112206 Test 22-60 | 4.8 | 28.74 | 0.00 | 1.97 | 0.00 | 0.55 | |
| 112206 Test 22-65 | 5.2 | 28.33 | 0.00 | 1.94 | 0.00 | 0.55 | |
| 112206 Test 22-70 | 5.6 | 28.72 | 0.00 | 1.97 | 0.00 | 0.56 | 0.00 |
| 112206 Test 22-75 | 6 | 28.80 | 0.00 | 1.97 | 0.00 | 0.56 | 0.00 |

Example 2

Figure 4:
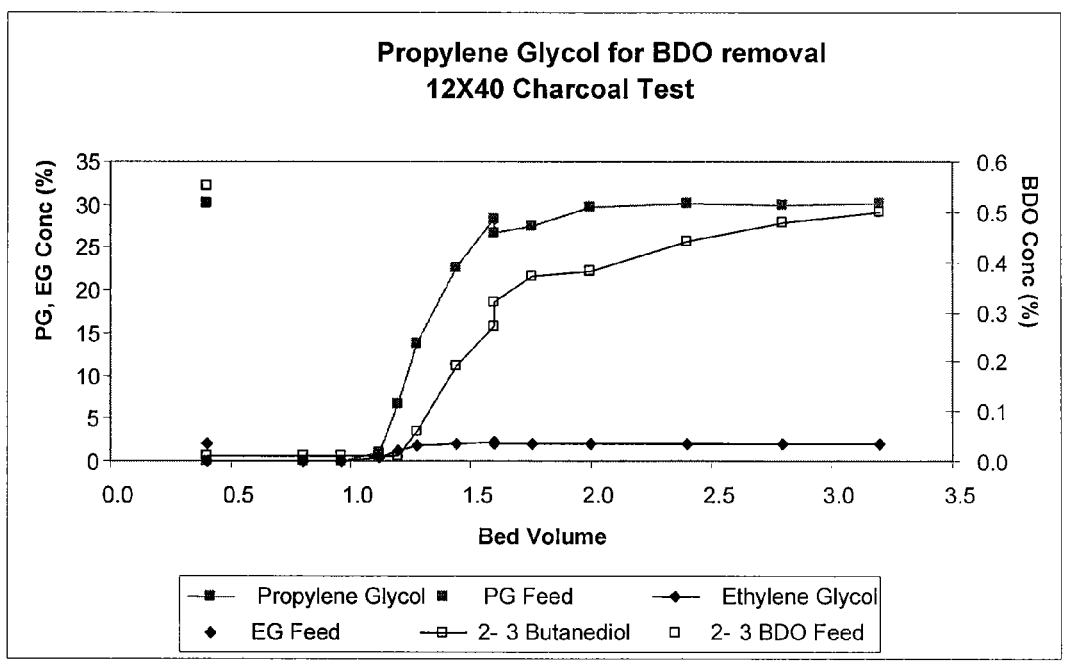
FIGS. 4 and 5 are plots illustrating the results of the experiments described in Example 2.
Figure 5:
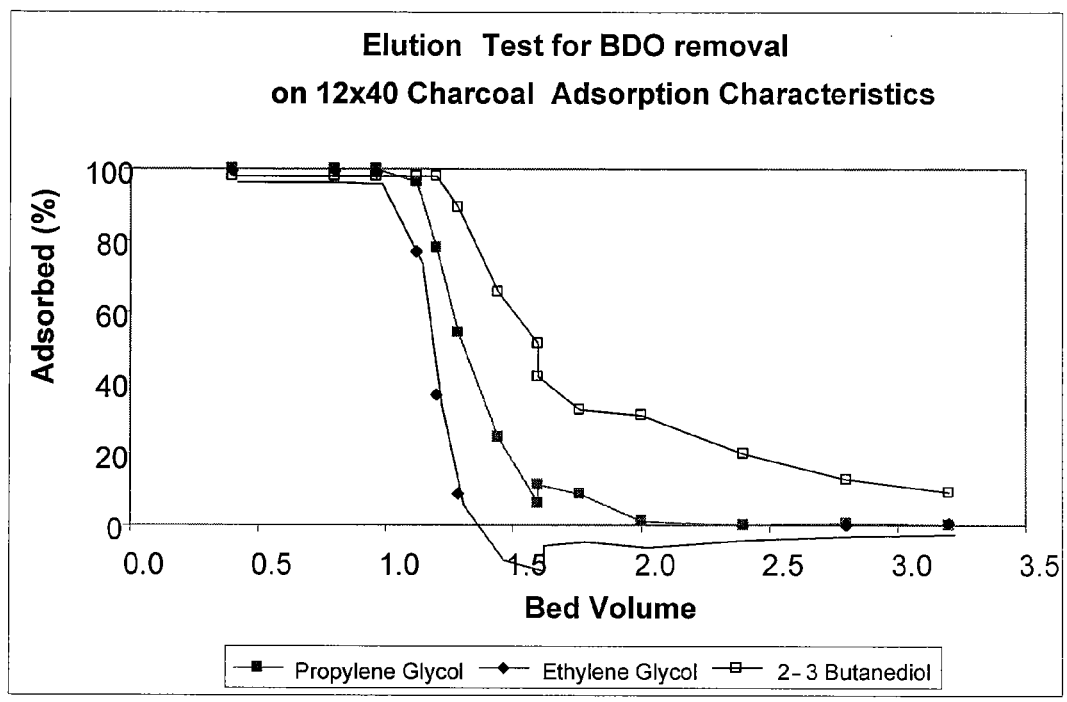

320 ml of a feed (PG reactor product) containing 30.12% 1,2-propanediol and 0.55% 2,3-butanediol was contacted with a 100 ml Calgon CPG 12×40 charcoal granular carbon bed in a column. Room temperature and flow rate of 5 ml/min was used. The results are shown in table below and indicate that the 2,3-BDO can be separated from other polyhydric alcohols using a carbon bed. FIGS. 4 and 5 graphically illustrate the results of this experiment. FIG. 4 is a breakthrough (capacity) plot showing the unadsorbed components relative to volumes of feed fed through the column, leading to breakthrough capacity. In FIG. 4, the horizontal axis is the bed volume ("BV"), the left vertical axis is the concentration in percentage of propylene glycol and ethylene glycol in the column effluent. The right vertical axis is butanediol concentration in the column effluent. FIG. 5 is a plot of a desorption (stripping) or regeneration test using 100% ethanol. In FIG. 5, the horizontal axis is the BV, and the vertical axis is the concentration, in percentage, of the propylene glycol and ethylene glycol which remained in the column bed using ethanol regeneration.

| Sample Id | Bed Volume | 1,2-Propanediol % | % Adsorbed | Ethylene Glycol % | % Adsorbed | 2,3-Butanediol % | % Adsorbed |
|---|---|---|---|---|---|---|---|
| 110806 Test 19-Feed | | 30.12 | 100.00 | 1.95 | 100.00 | 0.55 | 1.83 |
| 110806 Test 19-5 | 0.4 | 0.01 | 99.97 | 0.01 | 99.49 | 0.01 | 98.18 |
| 110806 Test 19-10 | 0.8 | 0.01 | 99.97 | 0.01 | 99.49 | 0.01 | 98.18 |
| 110806 Test 19-C12 | 0.96 | 0.01 | 99.97 | 0.02 | 98.97 | 0.01 | 98.18 |
| 110806 Test 19-C14 | 1.12 | 1.05 | 96.51 | 0.45 | 76.92 | 0.01 | 98.18 |
| 110806 Test 19-15 | 1.2 | 6.62 | 78.02 | 1.24 | 36.41 | 0.01 | 98.18 |
| 110806 Test 19-C16 | 1.28 | 13.80 | 54.18 | 1.78 | 8.72 | 0.06 | 89.09 |
| 110806 Test 19-C18 | 1.44 | 22.70 | 24.63 | 2.08 | −6.67 | 0.19 | 65.45 |
| 110806 Test 19-20 | 1.6 | 28.33 | 5.94 | 2.14 | −9.74 | 0.27 | 50.91 |
| 110806 Test 19-C22 | 1.6 | 26.63 | 11.59 | 2.00 | −2.56 | 0.32 | 41.82 |
| 110806 Test 19-C24 | 1.76 | 27.42 | 8.96 | 1.98 | −1.54 | 0.37 | 32.73 |
| 110806 Test 19-25 | 2 | 29.79 | 1.10 | 2.01 | −3.08 | 0.38 | 30.91 |
| 110806 Test 19-30 | 2.4 | 30.15 | −0.10 | 1.97 | −1.03 | 0.44 | 20.00 |
| 10106 Test 16-35 | 2.8 | 30.04 | 0.27 | 1.95 | 0.00 | 0.48 | 12.73 |
| 110806 Test 19-40 | 3.2 | 30.09 | 0.10 | 1.94 | 0.51 | 0.50 | 9.09 |

Example 3

Figure 8:
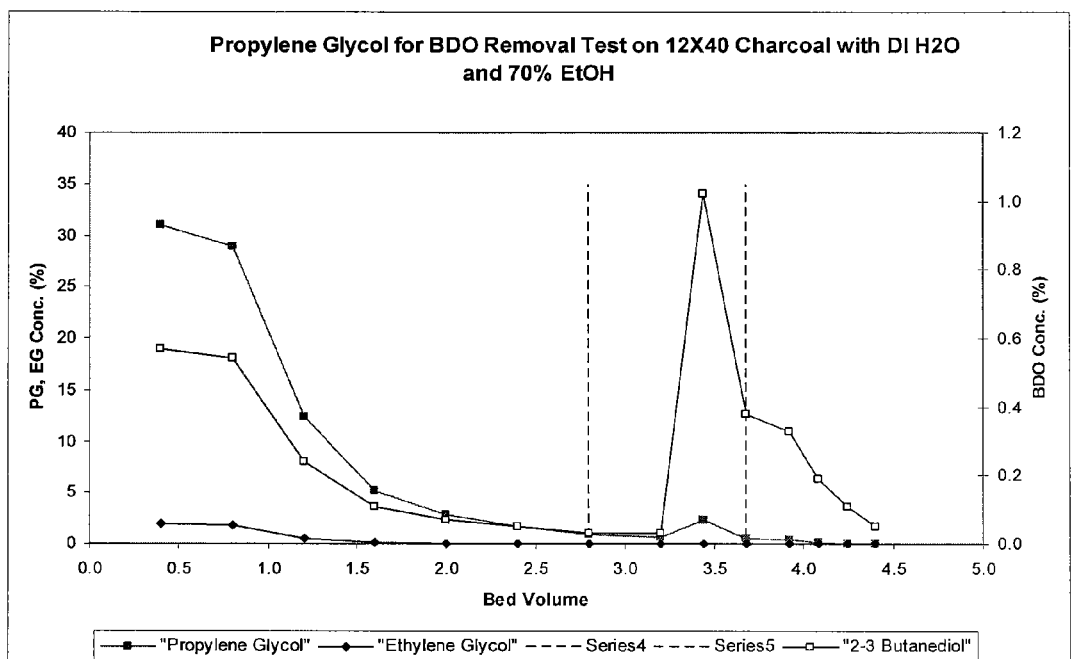
FIG. 8 is a plot illustrating the results of the experiments described in Example 3.

The butanediols adsorbed in example 2 were eluted from the chromatographic matrix with anhydrous ethanol. An eluate containing primarily 2,3-butanediol was obtained. The below results indicate that 2,3-butanediol can be eluted from an adsorption matrix such as a granular carbon bed to produce purified 2,3-butanediol after removal the eluting solvent by distillation. The results are also graphically illustrated in FIG. 8. The horizontal axis is the bed volume ("BV"), the left vertical axis is the concentration in percentage of propylene glycol and ethylene glycol that eluted from the column. The right vertical axis is butanediol concentration. In the table below, DI $H_2O$ indicates deionized water; 70% EtOH indicates a solution containing 70% ethanol and 30% water.

| Eluent | Sample Id | Bed Volume | 1,2-Propanediol % | Ethylene Glycol % | 2,3-Butanediol % |
|---|---|---|---|---|---|
| | Feed | | 30.12 | 1.95 | 0.55 |
| DI $H_2O$ | C5 | 0.4 | 31.01 | 1.98 | 0.57 |
| | C10 | 0.8 | 28.94 | 1.84 | 0.54 |
| | C15 | 1.2 | 12.39 | 0.58 | 0.24 |

-continued

| Eluent | Sample Id | Bed Volume | 1,2-Propanediol % | Ethylene Glycol % | 2,3-Butanediol % |
|---|---|---|---|---|---|
| | C20 | 1.6 | 5.17 | 0.11 | 0.11 |
| | C25 | 2 | 2.78 | 0.02 | 0.07 |
| | C30 | 2.4 | 1.68 | <0.01 | 0.05 |
| 70% | C35 | 2.8 | 0.94 | <0.01 | 0.03 |
| EtOH | C40 | 3.2 | 0.59 | <0.01 | 0.03 |
| | C43 | 3.44 | 2.36 | <0.01 | 1.02 |
| DI | C46 | 3.68 | 0.47 | <0.01 | 0.38 |
| H2O | C49 | 3.92 | 0.45 | <0.01 | 0.33 |
| | C51 | 4.08 | 0.13 | <0.01 | 0.19 |
| | C53 | 4.24 | 0.04 | <0.01 | 0.11 |
| | C55 | 4.4 | 0.02 | <0.01 | 0.05 |

Example 4

Several adsorbents were screened to determine their ability to remove BDO from a PG reactor product feed. 50 ml of a PG reactor product containing 0.51 percent 2,3-BDO was mixed with 10 ml of each adsorbent at 58 degrees C. for 1.5 hours. The mixture was agitated in a hot water bath to maintain temperature and subsequently filtered through a 0.45 micron filter to remove the adsorbent material. The amount of 2,3-BDO remaining in the treated PG reactor feed was measured. In certain cases about 8% of the 2,3-BDO was removed. The following table summarizes the results of this experiment.

| | % 2,3-BDO removed |
|---|---|
| Feed | 0.00 |
| LACHEMCO Spherical Alumina (20% Ag) | 0.00 |
| LACHEMCO Spherical Alumina (Neutral form) | 0.00 |
| LACHEMCO Spherical Alumina (Basic form) | 0.00 |
| LACHEMCO Spherical Alumina (Acidic form) | 0.00 |
| LACHEMCO Spherical Alumina (Cu+1 form) | 0.00 |
| Strong Acid Catalyst Lewatit S2620 | 1.00 |
| Carbon Powder BGHHM | 2.00 |
| Carbon Calgon CPG 20 × 50 | 5.00 |
| Carbon Coconut | 5.00 |
| Strong Acid Catalyst Lewatit S1468 | 1.00 |
| Strong Acid Catalyst Lewatit S2568 | 0.00 |
| Strong Acid Catalyst Lewatit S2568 (Cu+2 Form) | 0.00 |
| Strong Acid Catalyst Lewatit S2567 | 0.00 |
| Weak Acid Cation Lewatit TP 207 | 2.00 |
| Strong Base Anion Lewatit S6368 | 2.00 |
| Weak Base Anion Lewatit S4428 | 0.00 |
| Mol. Sieve 3A pore size | 0.00 |
| Adsorbent Mitsubishi AMP01 | 0.00 |
| Silica (20% Ag) | 0.00 |
| SILICA (12 × 40) | 0.00 |
| BENTONITE CLAY | 0.00 |
| Adsorbent XAD4 | 1.00 |
| Adsorbent XAD7 | 3.00 |
| Adsorbent Purolite MN 150 | 3.00 |
| Adsorbent Lewatit S7768 | 6.00 |
| Adsorbent Lewatit AF-5 | 8.00 |
| Adsorbent Ambersorb 563 | 2.00 |

Example 5

Figure 6:
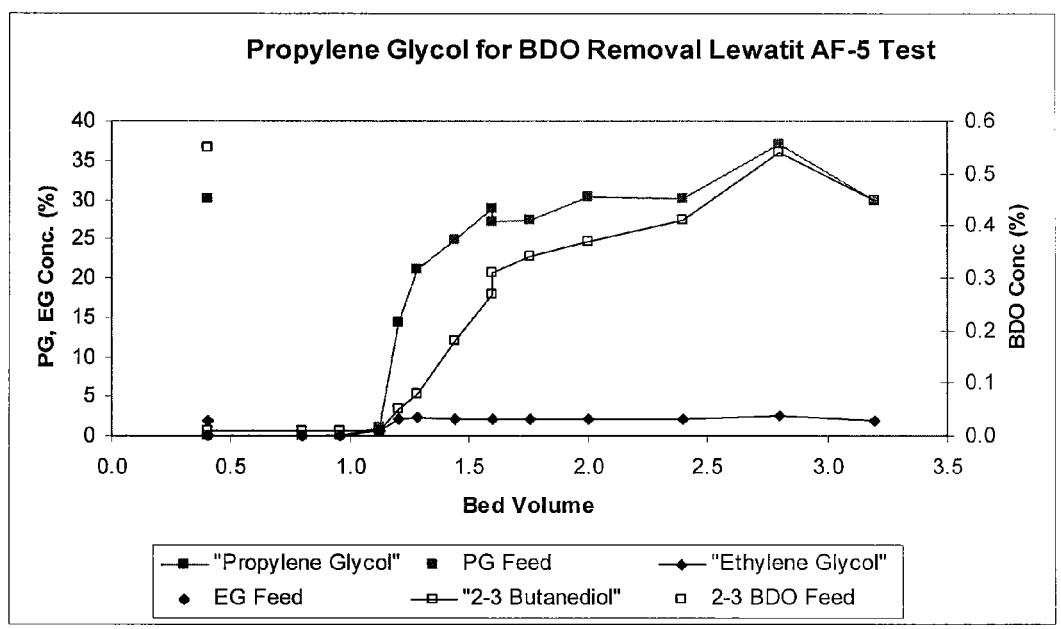
FIGS. 6 and 7 are plots illustrating the results of the experiments described in Example 5.
Figure 7:
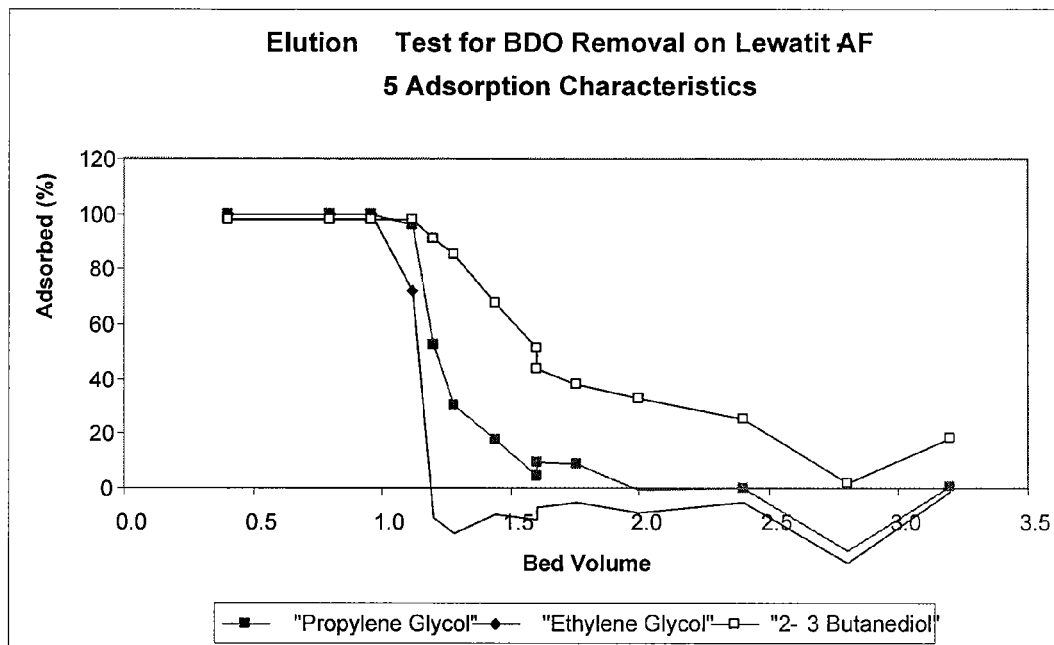

320 ml of a feed (PG reactor product) containing 30.12% 1,2 propanediol and 0.55% 2,3-butanediol was contacted with a 100 ml bed of the adsorbent Lewatit AF-5 substantially as in Example 2. The results are plotted in FIGS. 6 and 7, FIG. 6 is plot of a breakthrough (capacity) test and FIG. 7 is a plot of a desorption (stripping) or regeneration test. In FIG. 6, the horizontal axis is the bed volume ("BV"), the left vertical axis is the concentration in percentage of propylene glycol and ethylene glycol. The right vertical axis is butanediol concentration. In FIG. 7, the horizontal axis is the BV, and the vertical axis is the concentration, in percentage, of the propylene glycol and ethylene glycol which remained in the column bed using ethanol regeneration.

| Sample Id | Bed Volume | 1,2-Propanediol % | % Adsorbed | Ethylene Glycol % | % Adsorbed | 2,3-Butanediol % | % Adsorbed |
|---|---|---|---|---|---|---|---|
| 110806 Test 19-17 Feed | | 30.12 | 100.00 | 1.95 | 100.00 | 0.55 | 100.00 |
| 110806 Test 19-5 | 0.4 | 0.01 | 99.97 | 0.01 | 99.49 | 0.01 | 98.18 |
| 110806 Test 19-10 | 0.8 | 0.01 | 99.97 | 0.01 | 99.49 | 0.01 | 98.18 |
| 110806 Test 19-AF12 | 0.96 | 0.01 | 99.97 | 0.01 | 99.49 | 0.01 | 98.18 |
| 110806 Test 19-AF14 | 1.12 | 1.11 | 96.31 | 0.55 | 71.79 | 0.01 | 98.18 |
| 110806 Test 19-15 | 1.2 | 14.39 | 52.22 | 2.16 | −10.77 | 0.05 | 90.91 |
| 110806 Test 19-AF16 | 1.28 | 20.95 | 30.44 | 2.27 | −16.41 | 0.08 | 85.45 |
| 110806 Test 19-AF18 | 1.44 | 24.76 | 17.80 | 2.14 | −9.74 | 0.18 | 67.27 |
| 110806 Test 19-20 | 1.6 | 28.77 | 4.48 | 2.17 | −11.28 | 0.27 | 50.91 |
| 110806 Test | 1.6 | 27.21 | 9.66 | 2.09 | −7.18 | 0.31 | 43.64 |

-continued

| Sample Id | Bed Volume | 1,2-Propanediol % | % Adsorbed | Ethylene Glycol % | % Adsorbed | 2,3-Butanediol % | % Adsorbed |
|---|---|---|---|---|---|---|---|
| 19-AF22 110806 Test 19-AF24 | 1.76 | 27.40 | 9.03 | 2.05 | −5.13 | 0.34 | 38.18 |
| 110806 Test 19-25 | 2 | 30.24 | −0.40 | 2.12 | −8.72 | 0.37 | 32.73 |
| 110806 Test 19-30 | 2.4 | 30.14 | −0.07 | 2.05 | −5.13 | 0.41 | 25.45 |
| 10106 Test 16-35 | 2.8 | 37.06 | −23.04 | 2.48 | −27.18 | 0.54 | 1.82 |
| 110806 Test 19-40 | 3.2 | 29.88 | 0.80 | 1.98 | −1.54 | 0.45 | 18.18 |

Example 6

In the following example, PG reactor product was fed into a column containing Dow V493, a non-functional resin, substantially as in Example 2. In addition, a feed enriched in 2,3-butanediol in PG reactor product was prepared by mixing 1 mL pure 2,3-butanediol (Spectrum Chemical Co., Gardena, Calif.) into every 10 mL reactor product. The composition of the PG reactor product control feed ("not spiked") and enriched feed (spiked) with BDO, follows in the table below. PG: propylene glycol; EG: ethylene glycol; DEG: diethylene glycol; Na: sodium ion.

| Feed | PG % | 1,2-BDO % | 2,3-BDO % | Glycerol % | EG % | Lactic acid % | DEG % | Na ppm |
|---|---|---|---|---|---|---|---|---|
| Control | 25.47 | 0.31 | 1.65 | 0.15 | 1.49 | 2.35 | 0 | 5806 |
| 2,3-BDO enriched | 23.84 | 0.29 | 6.86 | 0.14 | 1.38 | 1.94 | 0 | 6612 |

Figure 10:
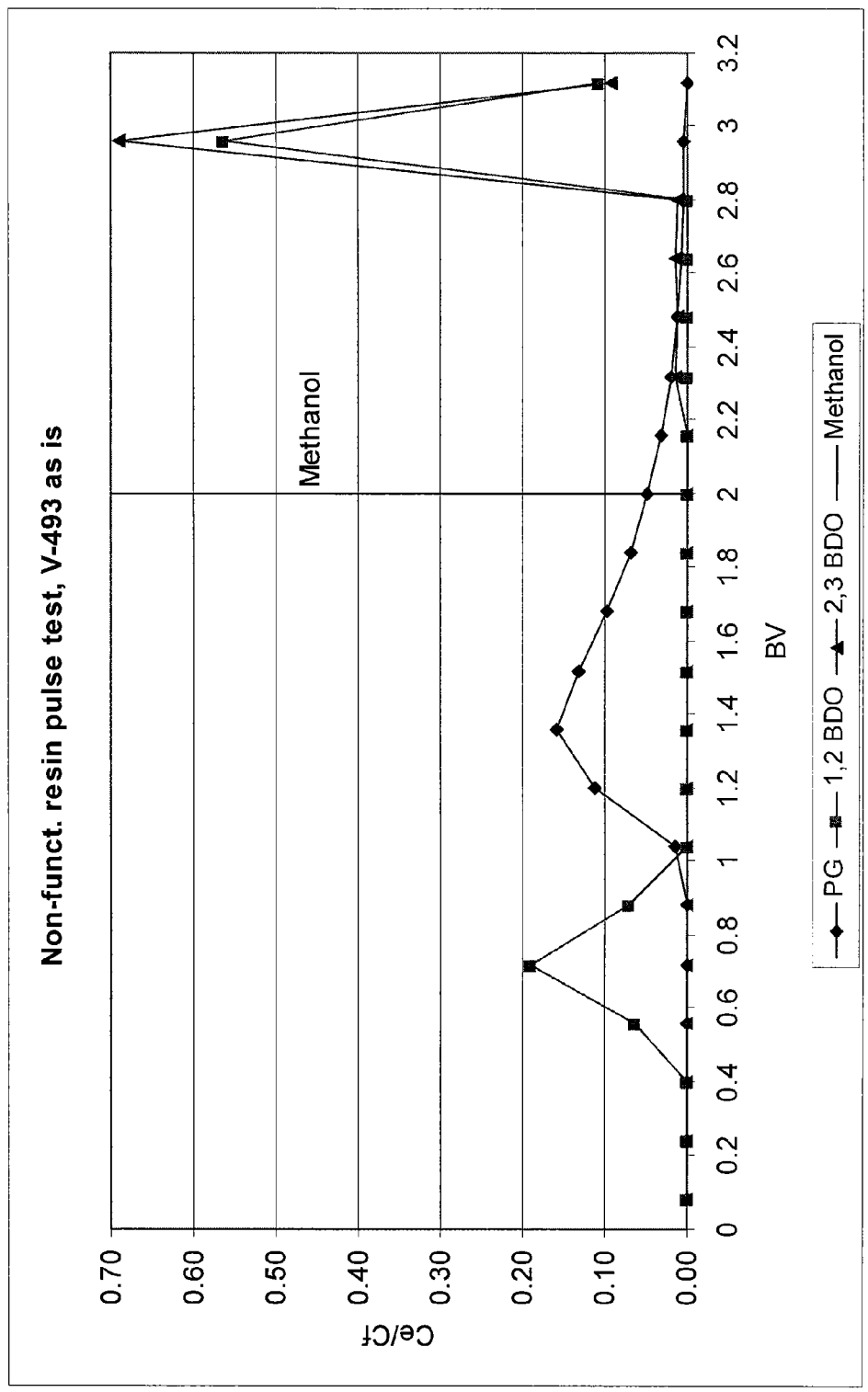

The results of the pulse tests are set forth in FIGS. 9 and 10. The reactor product was first eluted with deionized water (bed volumes 0-2), then methanol (bed volumes 2-3.12) The following abbreviations are used in the figures: BV=bed volume, PG=propylene glycol, BDO=butanediol, EG=ethylene glycol, DEG=diethylene glycol, Ce/Cf=the ratio of the concentration of the solute in the effluent and the concentration of the solute in the feed. FIG. 10 is a plot of Ce/Cf as a function of bed volume.

Example 7

A system for conducting simulated moving bed chromatography is prepared in a sequence of zones comprising 12 columns filled with Dowex V-493, a non-functional polymeric adsorbent resin, as the matrix, in a carousel in a simulated moving bed (SMB) apparatus (FIG. 11). Zone I is an adsorption zone; zone II is an enrichment zone; zone III is a desorption zone; zone IV is a solid regeneration zone; and zone V is a regeneration rinse zone (FIG. 11). The SMB apparatus contains 12 columns on a carousel arranged in zones comprising the following number of columns in zones I-V, respectively: 4-3-2-2-1. The SMB apparatus contains provisions for rotating the columns in the direction opposite the flow of fluid at defined intervals, called the "Step Time". The step time is 10 minutes. The SMB apparatus, together with the matrix and conduits bringing feed to the apparatus and conduits bringing products from the apparatus comprise a separation system.

Zone I (the Adsorption zone) is defined (bracketed) by the reactor product feed (propylene glycol, PG) inlet port and the recycled raffinate discharge port. There are 4 columns in this zone (columns 9-12 in FIG. 11). PG reactor product is applied continuously to the adsorption zone at 4 ml/min, joining the flow from the enrichment section from zone II in the SMB. Adsorption of several intermediately bound components (PG, and ethylene glycol (EG)), and highly bound components (2,3-BDO) takes place in the adsorption zone and a raffinate stream enriched in unbound and more lightly bound components, sodium hydroxide (NaOH), 1,2-BDO, and glycerol is continuously passed out of the SMB unit at the end of zone I as "Recycled Raffinate". This material containing glycerol and NaOH (with some 1,2-BDO and EG) can be recycled back to the PG reactor for conversion to PG.

Zone II (the Enrichment zone) is the zone defined (bracketed) by the product PG discharge port and the reactor product feed inlet port. There are 3 columns in this zone (columns 6-8 in FIG. 11). The flow in this zone is 33.9 ml/minute. The primary purpose of this zone is to increase the amount of PG bound to the matrix and allow it to displace the lightly bound components sodium hydroxide (NaOH), 1,2-BDO, and glycerol. This increases the PG product purity.

Zone III (the Desorption zone) is the zone bracketed by the Deionized (DI) elution water inlet port and the product PG discharge port. There are 2 columns in this zone (columns 4 & 5 in FIG. 11). The primary purpose of this zone is to desorb (strip) the PG product from the matrix. The DI elution water is pumped into this zone through the DI elution water inlet at 36.0 ml/minute, causing the PG to desorb from the matrix. At the end of the desorption zone, an effluent enriched in PG and depleted of NaOH, glycerol, EG and 1,2-BDO is continuously eluted from the SMB and allowed to pass out of the SMB through the product PG discharge port as an effluent labeled "Product PG".

Zone IV (the Regeneration zone) is the zone bracketed by the methanol inlet port and the raffinate (2,3-BDO) discharge port. There are 2 columns in this zone (columns 2 & 3 in FIG. 11). The primary purpose of this zone is to desorb (strip) the tightly bound components (2,3-BDO) and other potential fouling compounds from the matrix. The flow in this zone is 36.0 ml/minute. 2,3-BDO is allowed to pass out of the SMB through the raffinate discharge port as an effluent labeled "Raffinate (2,3-BDO)".

Zone V (the Regeneration Rinse zone) is the zone bracketed by the DI water inlet port and the methanol inlet port. There is 1 column in this zone (column 1 in FIG. 11). The primary purpose of this zone is to remove the methanol as mobile phase and prepare the matrix for the Adsorption zone (zone I). The flow into this zone is 15.0 ml/minute, which is sufficient to displace the void fraction methanol from the column.

The separation of three effluents, each enriched in a separate component through ports in FIG. 11 shows that operation of the SMB in this manner allows ternary separation (ternary desorption") of the feed into effluents enriched in separate compounds. The effluent (raffinate) from column 3 is enriched in 2,3-BDO; the effluent from column 5 is enriched in propylene glycol; the effluent from column 12 ("Recycled raffinate") is enriched in sodium hydroxide (NaOH), 1,2-BDO, and glycerol.

Example 8

The simulated moving bed chromatography is configured in a 1-1-3-3-4 sequence in a simulated moving bed (SMB) apparatus. The matrix used is Mitsubishi SP700, non-functional polymeric adsorbent resin. Zone I is an adsorption zone; zone II is an enrichment zone; zone III is a desorption zone; zone IV is a solid regeneration zone; and zone V is a regeneration rinse zone (FIG. 12). The SMB apparatus contains 12 columns on a carousel, and provisions for rotating the columns in the direction opposite the flow of fluid at defined intervals, called the "Step Time". The step time is 10 minutes.

Zone I (the Adsorption zone) is defined by the feed, propylene glycol (PG) inlet and the Product PG discharge ports. There are 4 columns in this zone (columns 9-12 in FIG. 12). PG reactor product, enriched with BDO or control is applied continuously in the adsorption zone at 9.6 ml/min, joining the flow in the SMB. The components of the feed material chromatographically move through the columns in the zone such that PG, ethylene glycol (EG), and lightly bound and unbound components such as sodium hydroxide (NaOH), 1,2-BDO, and glycerol are continuously passed out of the SMB unit at the end of zone I as "PG Product" and the 2,3-BDO component is retained with the solid phase.

Zone II (the Depletion zone) is the zone defined by the Raffinate 1 discharge and the feed inlet ports (columns 6-8 in FIG. 12). The flow in this zone is 38.4 ml/minute. There are 3 columns in this zone. The primary purpose of this zone is to deplete the matrix loading of PG and enrich it with the butanediol components.

Zone III (the Desorption zone) is the zone defined by the Deionized (DI) water elution inlet and the Raffinate 1 discharge ports (columns 3, 4 & 5 in FIG. 12). There are 3 columns in this zone. The primary purpose of this zone is to strip the butanediol components from the resin matrix. The DI water elution is pumped into this zone through the DI water inlet at 48.0 ml/minute, and it strips BDO from the matrix. At the end of the desorption zone, an effluent enriched in BDO and depleted of PG, EG, and glycerol is continuously eluted from the SMB and allowed to pass out of the SMB as an effluent labeled "Raffinate 1".

Zone IV (the Regeneration zone) is the zone defined by the Raffinate 1 (BDO) discharge and methanol inlet ports (column 2 in FIG. 12). There is 1 column in this zone. The primary purpose of this zone is to strip the tightly bound components (1,2-BDO and 2,3-BDO) from the matrix and to remove other potential fouling compounds that were adsorbed. The flow in this zone is 30.0 ml/minute.

Zone V (the Regeneration rinse zone) is the zone defined by the DI water inlet and methanol inlet ports (column 1 in FIG. 12). There is 1 column in this zone. The primary purpose of this zone is to remove the methanol as mobile phase and prepare the matrix for the adsorption zone (zone I). The flow in this zone is 19.2 ml/minute, which is just about enough to displace the void fraction methanol from the column.

Example 9

Figure 13:
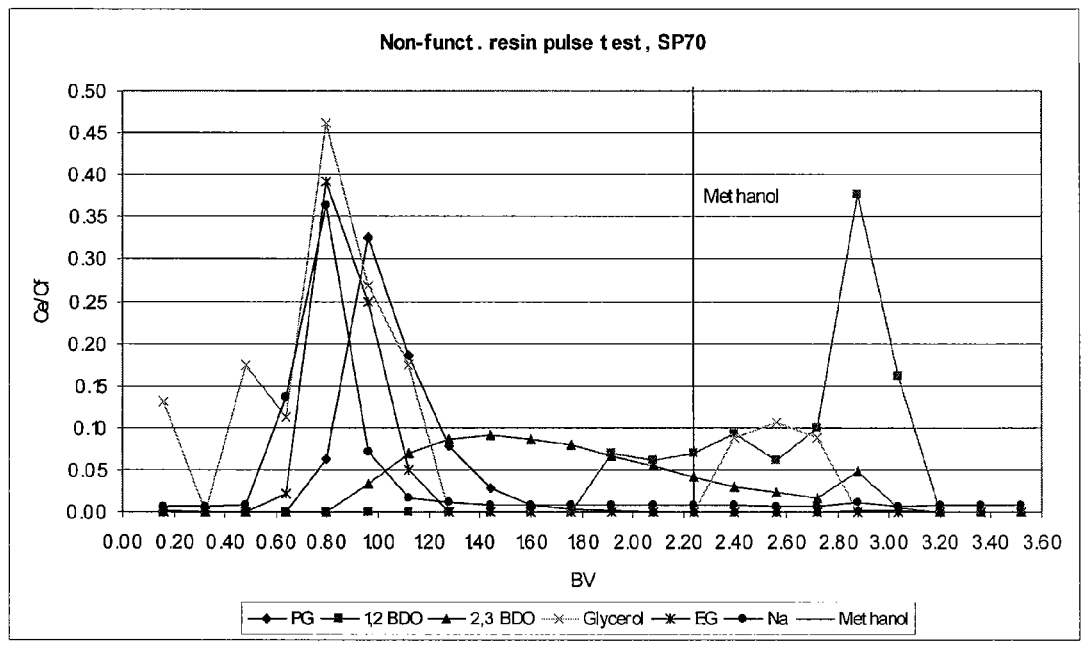
FIG. 13 is a plot illustrating the results of the experiments described in Example 9.

In a pulse test, 10 ml of a feed containing 23.28% 1,2-propanediol and 6.45% 2,3-butanediol was contacted with 100 ml Sepabeads SP70 resin matrix (Mitsubishi) substantially as in Example 2. Column temperature was set at 45 degrees C. The feed was eluted with deionized water at a flow rate of 3 mL/min for approximately 2 bed volumes (200 mL). At approximately 2 bed volumes, the deionized water eluent was replaced with 99% methanol eluent. The results are shown in FIG. 13. Ternary separation could be effected by setting up the Simulated Moving Bed device to collect the fraction eluting at 0.4 to 1.4 BV to obtain an effluent enriched in sodium, glycerol ethylene glycol, and propylene glycol; a second fraction eluting at 1.4 to 2.2 bed volumes to obtain an effluent enriched in 2,3-BDO; and a third fraction eluting at 2.2 to 3.2 BV to obtain a fraction enriched in 1,2-BDO.

Example 10

Figure 14:
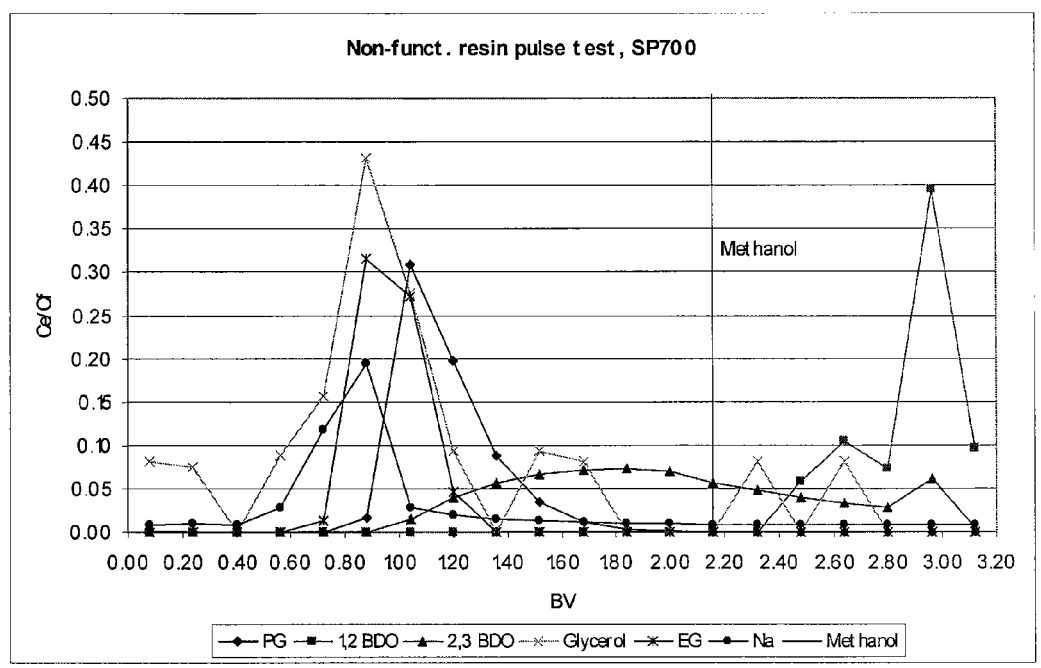
FIG. 14 is a plot illustrating the results of the experiments described in Example 10.

In a pulse test, 10 ml of a feed containing 23.69% 1,2-propanediol and 6.58% 2,3-butanediol was contacted with 100 ml Sepabeads SP700 resin (Mitsubishi) substantially as in Example 2. Column temperature was set at 45 degrees C. The feed was eluted with deionized water at a flow rate of 3 mL/min for approximately 2 bed volumes (200 mL). At approximately 2 bed volumes, the deionized water eluent was replaced with 99% methanol eluent. The results are shown in FIG. 14.

Example 11

Figure 15:
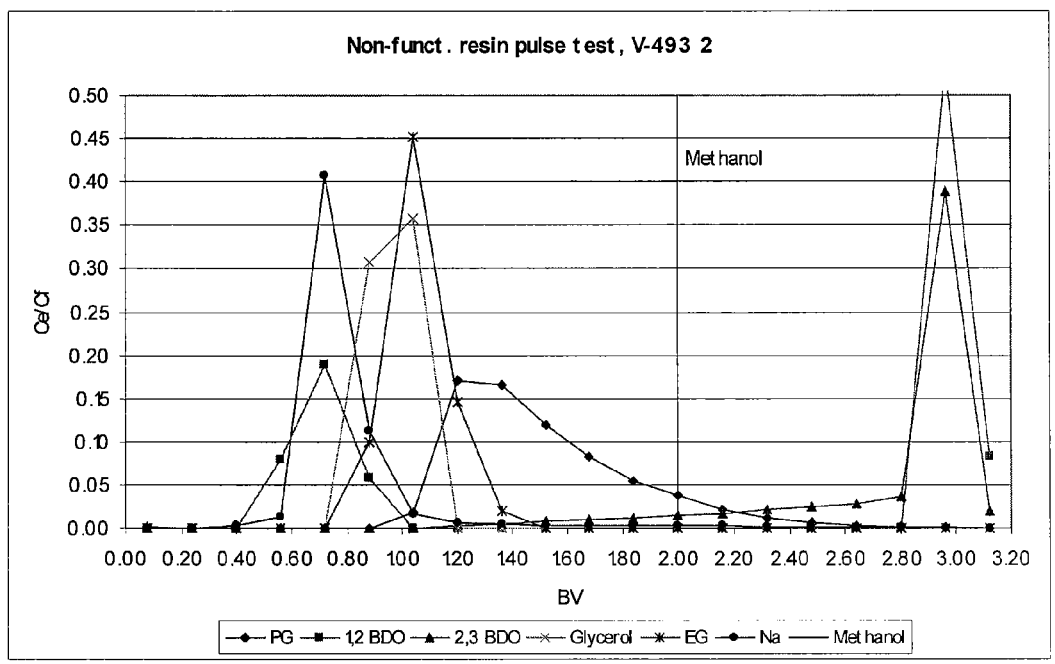
FIG. 15 is a plot illustrating the results of the experiments described in Example 11.

In a pulse test, 10 ml of a feed containing 23.84% 1,2-propanediol with 2,3-butanediol added to the feed to enrich the concentration up to 6.86% 2,3-butanediol (substantially as in example 6) was contacted with 100 ml Dowex Optipore V493 resin matrix (Dow) substantially as in Example 2. Column temperature was set at 45 degrees C. The feed was eluted with deionized water at a flow rate of 3 mL/min for approximately 2 bed volumes (200 mL). At approximately 2 bed volumes, the deionized water eluent was replaced with 99% methanol eluent. The results are shown in FIG. 15. In this example, the portion of the figure from 0 to 2.0 bed volumes depicts separation in a chromatographic mode, in which separation is based on the differences in affinity between the chromatographic bed and the components in the mixture, which causes retardation of certain substances relative to others in a given eluent (deionized water). In an SMB apparatus as depicted in FIG. 11, these components will be separated and elute in Zones I-III (columns 4-12) through two separate outlet ports. A first outlet port will remove the fraction in bed volumes 0 to 0.9, to provide an effluent enriched in sodium and 1,2-BDO. A second outlet port will remove the fraction from 0.9 to 2.0 bed volumes to provide an effluent enriched in ethylene glycol and propylene glycol. The portion of the figure from 2.0 to 3.2 bed volumes depicts separation in an adsorb/desorb mode. In this mode, the BDO components (some of the 1,2-BDO and all of the 2,3-BDO) were much more retarded in the flow of deionized water eluent, and did not elute from the column with water in the first two bed volumes (FIG. 15). The application of a desorbing elution solvent (methanol) allowed the BDO components to be eluted from the column. In an SMB apparatus as depicted in FIG. 11, these components will be separated and eluted in Zones IV and V (columns 1-3).

Example 12

Figure 16:
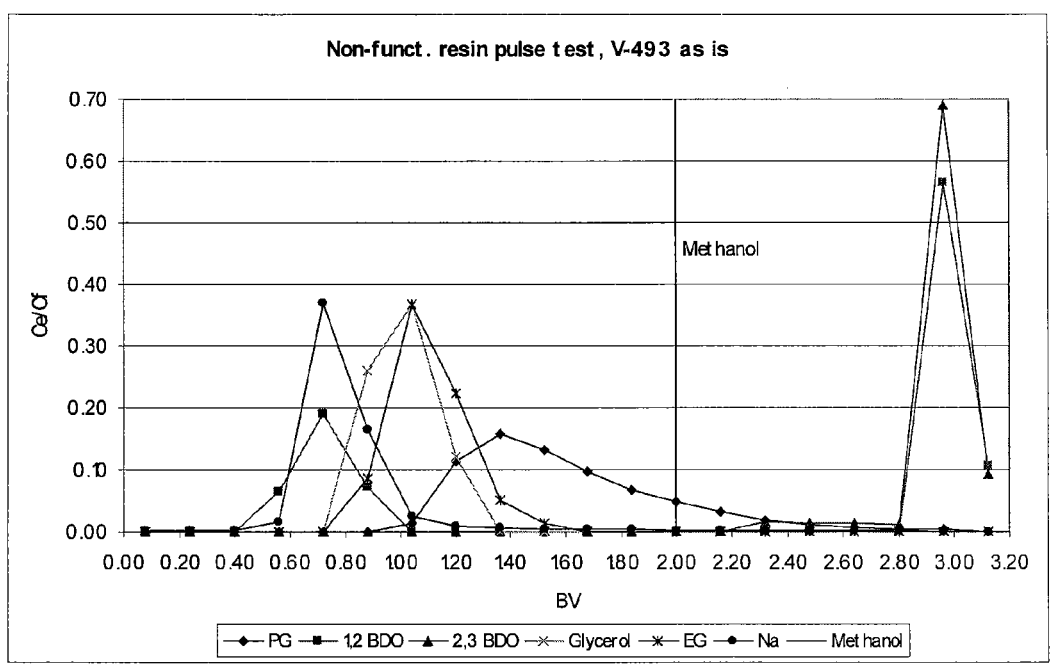
FIG. 16 is a plot illustrating the results of the experiments described in Example 12.

In a pulse test, 10 ml of a feed containing 25.47% 1,2-propanediol and 1.65% 2,3-butanediol was contacted with 100 ml Dowex Optipore V493 resin (Dow) substantially as in Example 2. Column temperature was set at 45 degrees C. The feed was eluted with de ionized water at a flow rate of 3 mL/min for approximately 2 bed volumes (200 mL). At approximately 2 bed volumes, the deionized water eluent was replaced with 99% methanol eluent. The results are shown in FIG. 16. In this example, the portion of the figure from 0 to 2.0 bed volumes depicts separation in a chromatographic mode, in which separation is based on the differences in affinity between the chromatographic bed and the components in the mixture, which causes retardation of certain substances relative to others in a given eluent (deionized water). In an SMB apparatus as depicted in FIG. 11, these components will be separated and eluted in Zones I-III (columns 4-12). The portion of the figure from 2.0 to 3.2 bed volumes depicts separation in an adsorb/desorb mode. In this mode, the BDO components (1,2-BDO and 2,3-BDO) were much more retarded in the flow of deionized water eluent, and did not elute from the column with water in the first two bed volumes (FIG. 16). The application of a desorbing elution solvent (methanol) allowed the BDO components to be eluted from the column. In an SMB apparatus as depicted in FIG. 11, these components will be separated and eluted in Zones IV and V (columns 1-3).

Example 13

Figure 17:
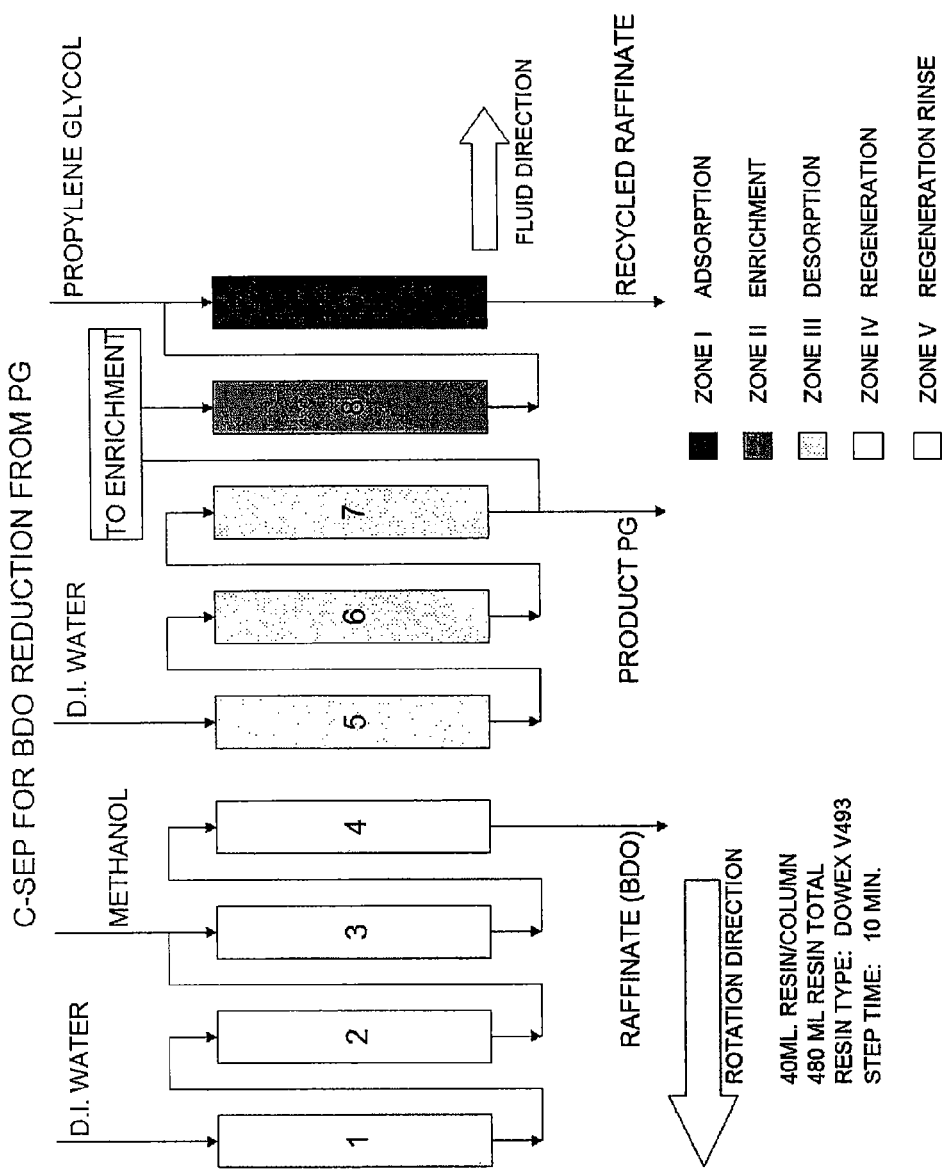
FIG. 17 is a diagram illustrating the simulated moving bed chromatography apparatus configured in the 2-2-3-1-1 sequence described in Example 13.

In one embodiment the simulated moving bed chromatography was configured in a 2-2-3-1-1 sequence in a simulated moving bed (SMB) apparatus (FIG. 17) and filled with Dowex V-493, a non-functional polymeric adsorbent resin, as the matrix. The matrix was arranged in zones. Zone I was an adsorption zone; zone II was an enrichment zone; zone III was a desorption zone; zone IV was a solid regeneration zone; and zone V was a regeneration rinse zone (FIG. 17). The SMB apparatus contained 9 columns on a carousel, and provisions for rotating the columns in the direction opposite the flow of fluid at defined intervals, called the "Step Time". The step time was 10 minutes.

Zone I (the Adsorption zone) was defined (bracketed) by the reactor product feed (propylene glycol, PG) inlet port and the recycled raffinate discharge port. There was 1 column in this zone (column 9 FIG. 17). PG reactor product was applied continuously to the adsorption zone at 0.86 ml/min, joining the flow from the enrichment section from zone II in the SMB. Adsorption of several intermediately bound components (PG, and ethylene glycol (EG)), and highly bound components (2,3-BDO) took place in the adsorption zone and a raffinate stream enriched in unbound and more lightly bound components, sodium hydroxide (NaOH), 1,2-BDO, and glycerol was continuously passed out of the SMB unit at the end of zone I as "Recycled Raffinate". This material containing glycerol and NaOH (with some 1,2-BDO and EG) can be recycled back to the PG reactor for conversion to PG.

Zone II (the Enrichment zone) was the zone defined (bracketed) by the product PG discharge port and the reactor product feed inlet port. There was 1 column in this zone (column 8 in FIG. 17). The flow in this zone was 1.2 ml/minute. The primary purpose of this zone was to increase the amount of PG bound to the matrix and allow it to displace the lightly bound components sodium hydroxide (NaOH), 1,2-BDO, and glycerol. This increased the PG product purity.

Zone III (the Desorption zone) was the zone bracketed by the Deionized (DI) elution water inlet port and the product PG discharge port. There were 3 columns in this zone (columns 4-7 in FIG. 17). The primary purpose of this zone was to desorb (strip) the PG product from the matrix. The DI elution water was pumped into this zone through the DI elution water inlet at 4.4 ml/minute, causing the PG to desorb from the matrix. At the end of the desorption zone, an effluent enriched in PG and depleted of NaOH, glycerol, EG, 2,3-BDO, and 1,2-BDO was continuously eluted from the SMB and allowed to pass out of the SMB through the product PG discharge port as an effluent labeled "Product PG".

Zone IV (the Regeneration zone) was the zone bracketed by the methanol inlet port and the raffinate (BDO) discharge port. There were 2 columns in this zone (columns 3 & 4 in FIG. 17). The primary purpose of this zone was to desorb (strip) the tightly bound components (BDO) and other potential fouling compounds from the matrix. The flow of methanol into this zone was 6 ml/minute. BDO was allowed to pass out of the SMB through the raffinate discharge port as an effluent labeled "Raffinate BDO".

Zone V (the Regeneration Rinse zone) was the zone bracketed by the DI water inlet port and the methanol inlet port. There were 2 columns in this zone (columns 1 & 2 in FIG. 17). The primary purpose of this zone was to remove the methanol as mobile phase and prepare the matrix for the Adsorption zone (zone I). The flow of DI water into this zone was 4.4 ml/minute, which was sufficient to displace the void fraction methanol from the column.

The separation of three effluents, each enriched in a separate component through ports in FIG. 17 showed that operation of the SMB in this manner allowed ternary separation (ternary desorption") of the feed into effluents enriched in separate compounds. The effluent (raffinate) from column 4 was enriched in 1,3 butanediol; the effluent from column 7 was enriched in propylene glycol; the effluent from column 9 ("Recycled raffinate") was enriched in 1,2-butanediol, and also contained ethylene glycol, sodium hydroxide (NaOH), and glycerol.

What is claimed is:

1. A method of separating at least one butanediol compound from a mixture of polyhydric alcohols containing at least one butanediol compound and at least one non-butanediol compound, comprising propylene glycol, ethylene glycol or a mixture thereof comprising contacting the mixture with a matrix, wherein the at least one butanediol compound or the at least one non-butanediol compound adsorbs to the matrix.

2. The method of claim 1, wherein the at least one butanediol compound adsorbs to the matrix.

3. The method of claim 2, wherein a second butanediol compound adsorbs to the matrix.

4. The method of claim 3, wherein an effluent enriched in a non-butanediol compound, an effluent enriched in a first butanediol compound, and an effluent enriched in a second butanediol compound are produced.

5. The method of claim 4, further comprising:
   (a) recovering an effluent enriched in propylene glycol;
   (b) recovering an effluent enriched in 1,2-butanediol; and,
   (c) recovering an effluent enriched in 2,3-butanediol.

6. The method of claim 1, wherein the at least one butanediol compound comprises 1,2-butanediol, 2,3-butanediol, or a mixture thereof.

7. The method of claim 1, wherein the matrix comprises a material selected from the group consisting of carbon black, granular carbon, carbon powder, activated charcoal, non-activated charcoal, diatomaceous earth, silica, alumina, clay, and resin material.

8. The method of claim 7, wherein the matrix is a granular carbon.

9. The method of claim 7, wherein the matrix is a resin material.

10. The method of claim 9, wherein the resin is a carbon-based macroporous resin.

11. The method of claim 1, wherein the matrix is a chromatographic matrix or an adsorptive matrix.

12. The method of claim 11, wherein the matrix is contacted with the mixture of polyhydric alcohols containing at least one butanediol compound and at least one non-butanediol compound in a simulated moving bed apparatus.

13. The method of claim 12, wherein the mixture of polyhydric alcohols comprises propylene glycol and wherein an extract or product stream enriched in propylene glycol and depleted of butanediol compounds, and a raffinate depleted of propylene glycol and enriched in butanediol compounds relative to a feed stream are produced.

14. The method of claim 13, further comprising recovering a recycled raffinate depleted of propylene glycol and enriched in ethylene glycol relative to a feed stream.

15. The method of claim 11, wherein the contacting comprises flowing the mixture of polyhydric alcohols over or through a chromatographic matrix or an adsorptive matrix arranged in a series of columns.

16. The method of claim 15, wherein said series comprises one or more zones, wherein each zone comprises one or more said chromatographic beds, columns or parts thereof.

17. The method of claim 16, wherein said one or more zones comprises the following zones:
(a) an adsorption zone;
(b) an enrichment zone;
(c) a desorption zone;
(d) a regeneration zone; and,
(e) a regeneration rinse zone;
and wherein each zone is defined by the primary function of one or more chromatographic beds, columns or parts thereof.

18. The method of claim 1, wherein the matrix is a non-functional resin.

* * * * *